Figure 1B:
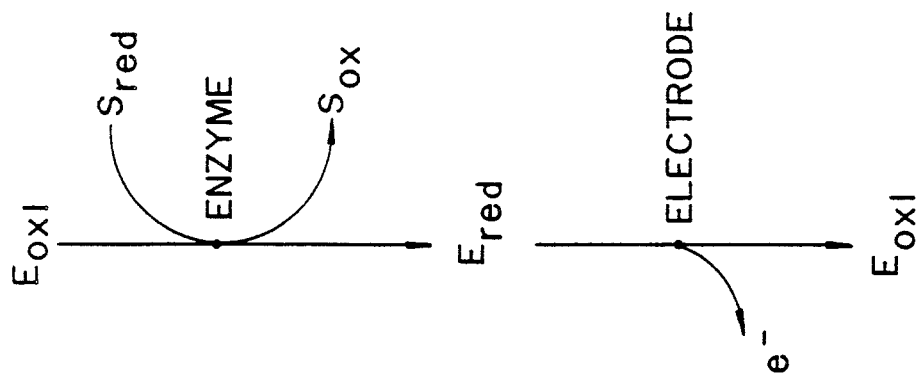

United States Patent [19]

Hoenes et al.

[11] Patent Number: 5,122,244
[45] Date of Patent: Jun. 16, 1992

[54] METHOD AND SENSOR ELECTRODE SYSTEM FOR THE ELECTROCHEMICAL DETERMINATION OF AN ANALYTE OR AN OXIDOREDUCTASE AS WELL AS THE USE OF SUITABLE COMPOUNDS THEREFOR

[75] Inventors: Joachim Hoenes, Zwingenberg; Jurgen Schaeffler, Weinheim, both of Fed. Rep. of Germany

[73] Assignee: Boehringer Mannheim GmbH, Mannheim, Fed. Rep. of Germany

[21] Appl. No.: 650,265

[22] Filed: Feb. 4, 1991

[30] Foreign Application Priority Data

Feb. 3, 1990 [DE] Fed. Rep. of Germany ....... 4003194

[51] Int. Cl.$^5$ .......................... C12Q 1/54; G01N 27/26
[52] U.S. Cl. ............................................... 204/153.12
[58] Field of Search ........................... 204/153.12, 403

[56] References Cited

U.S. PATENT DOCUMENTS

| | | | |
|---|---|---|---|
| 4,045,297 | 8/1977 | Weeks et al. | 204/153.12 |
| 4,220,503 | 9/1980 | Johnson | 204/153.12 |
| 4,224,125 | 9/1980 | Nakamura et al. | 204/153.12 |
| 4,297,173 | 10/1981 | Hikuma et al. | 204/153.12 |
| 4,304,853 | 12/1981 | Jozefonvicz et al. | 204/153.12 |
| 4,490,464 | 12/1984 | Gorton et al. | 204/153.12 |
| 4,882,013 | 11/1989 | Turner et al. | 204/153.12 |
| 4,927,516 | 5/1990 | Yamaguchi et al. | 204/153.12 |
| 4,948,727 | 8/1990 | Cass et al. | 204/153.12 |

OTHER PUBLICATIONS

P. W. Carr et al., "Theory and Applications of Enzyme Electrodes in Analytical and Clinical Chemistry", pp. 197-310 (1980).

J. J. D'Amico et al., *J. Amer. Chem. Soc'y.*, 81, 5957 (1959).
Nishino et al., *Chemical Abstracts*, 57, 13922 (1962).
Freifelder et al., *J. Org. Chem.*, 26, 1477 (1961).
Perry et al., *Can. J. Res.*, 14, (b), 81 (1936).
Stewart et al., *J. Org. Chem.*, 13, 134 (1948).
Kremer, *J. Amer. Chem. Soc'y.*, 58, 379 (1963).
H. Howell et al., *J. Org. Chem.*, 27, 1709 (1962).
M. S. Kharash et al., *J. Org. Chem.*, 8, 189 (1943).
Azheer et al., *Indian J. Chem.*, 1, 479 (1963).
March, *Advanced Organic Chemistry*, 20-23 and 246-249 (1977).

Primary Examiner—John Niebling
Assistant Examiner—Bruce F. Bell
Attorney, Agent, or Firm—Nikaido, Marmelstein, Murray & Oram

[57] ABSTRACT

The subject matter of the invention is a method for the electrochemical determination of an analyte in the presence of an oxidoreductase and a reducible substance which transfers electrons which arise during the course of the determination reaction from the oxidoreductase onto an electrode and thus leads to a signal which is a measure for the analyte to be determined whereby the reducible substance is enzymatically reduced and oxidized at the electrode, which is characterized in that the substance which forms at the electrode by oxidation is different from the reducible substance used initially, as well as a corresponding sensor electrode system and the use of compounds suitable therefor. Finally new nitrosoaniline derivatives and a process for their production are also subject matter of the invention.

9 Claims, 11 Drawing Sheets

Fig.2a
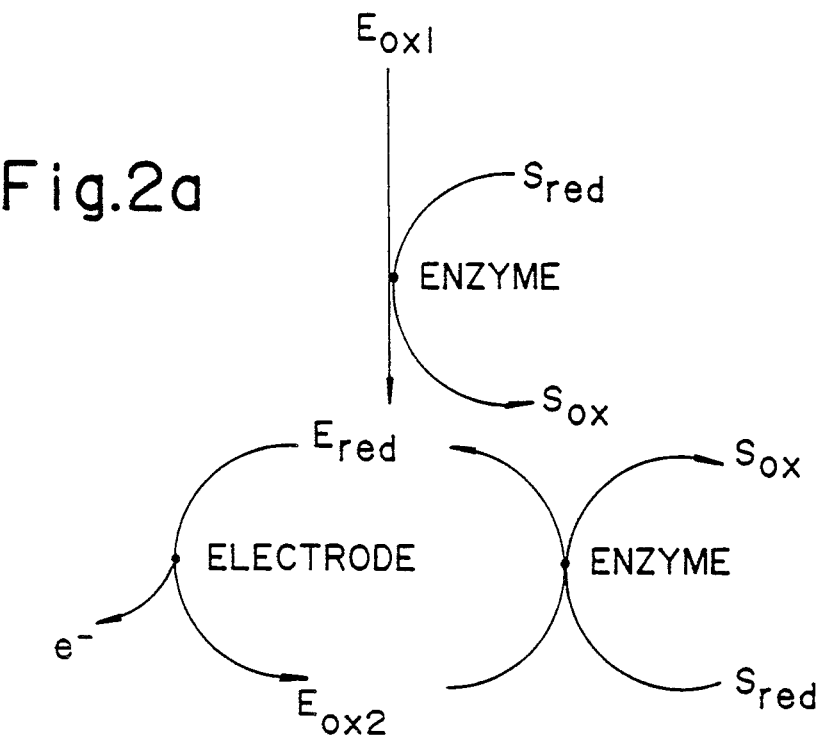
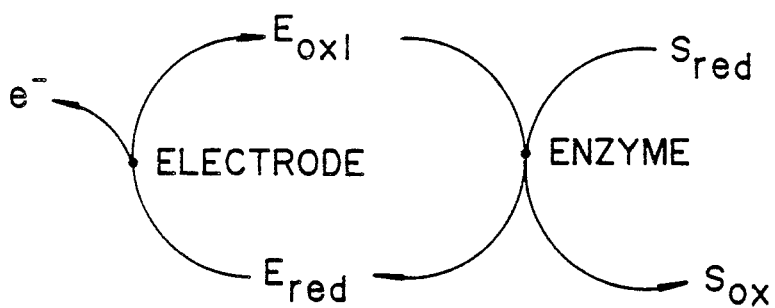
Fig.2b

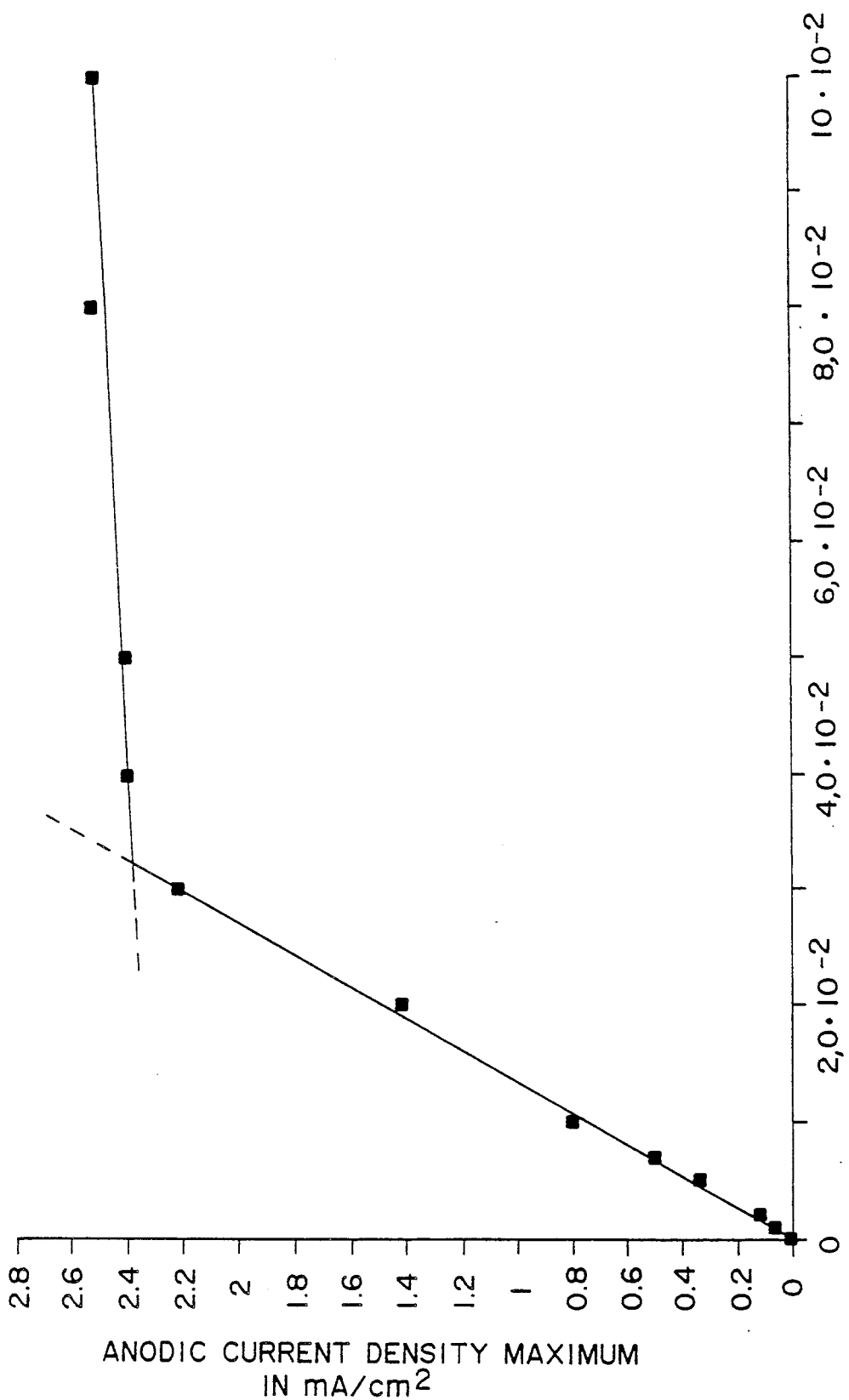

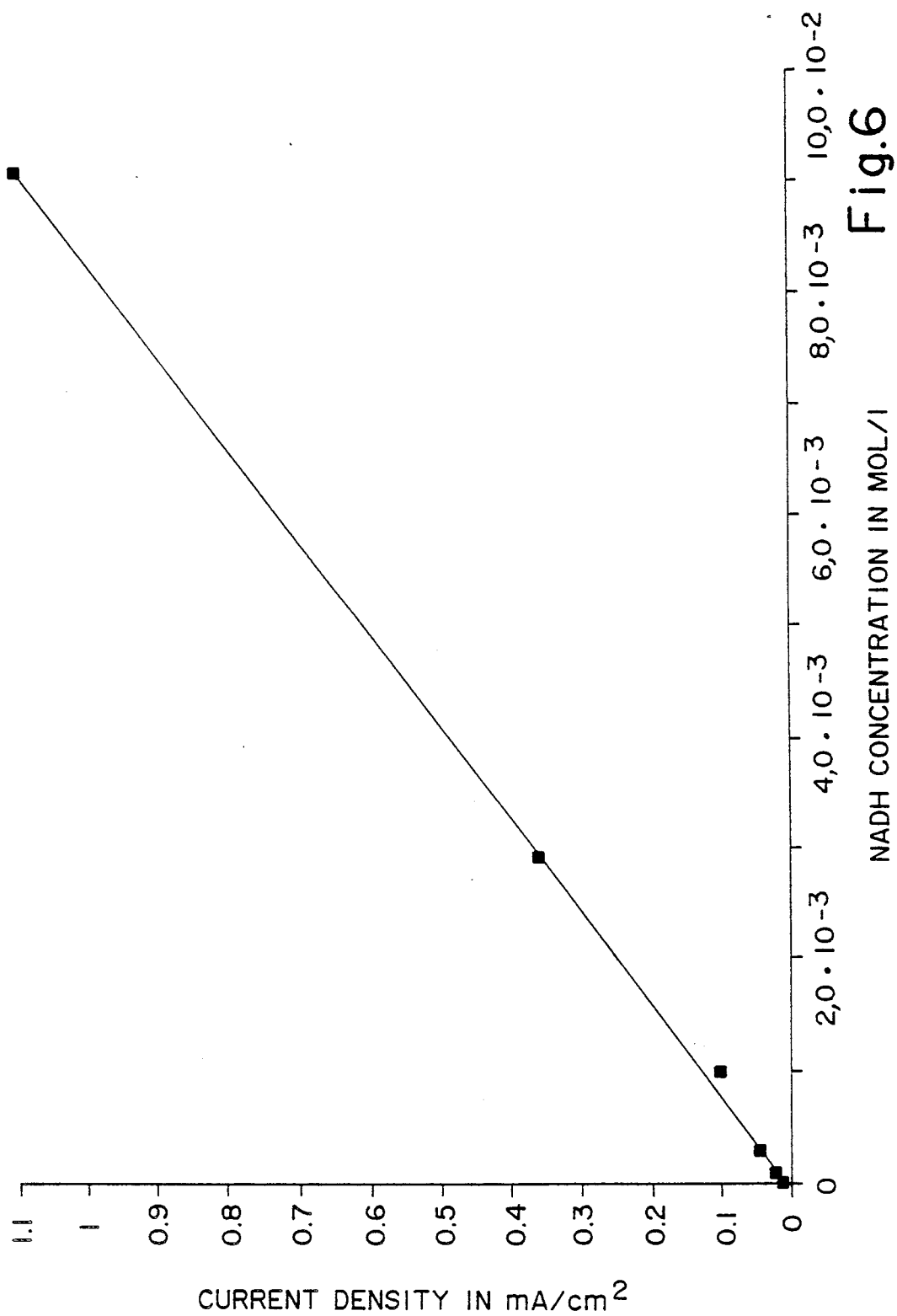

METHOD AND SENSOR ELECTRODE SYSTEM FOR THE ELECTROCHEMICAL DETERMINATION OF AN ANALYTE OR AN OXIDOREDUCTASE AS WELL AS THE USE OF SUITABLE COMPOUNDS THEREFOR

The invention concerns a method for the electrochemical determination of an analyte in the presence of an oxidoreductase and a reducible substance which transfers electrons which arise during the course of the determination reaction from the oxidoreductase onto an electrode and thus leads to a signal which is a measure for the analyte to be determined, whereby the reducible substance is enzymatically reduced and oxidized at the electrode, or a corresponding process for the electrochemical determination of an oxidoreductase in the presence of an enzyme substrate and a reducible substance as characterized above.

In addition, the invention concerns a sensor electrode system for the electrochemical determination of an analyte in a sample containing at least two electrically conductive agents each of which are present isolated from one another and which can be brought into electrical contact with the sample to be examined by means of an electrically conductive surface in which at least one of the electically conductive surfaces contacts an oxidoreductase and a reducible substance which is capable of transferring electrons between the oxidoreductase and the electrically conductive surface, or a corresponding sensor electrode system for the determination of an oxidoreductase in which at least one of the electrically conductive surfaces contacts an oxidoreductase substrate and a reducible substance as characterized above.

Finally the invention concerns the use of certain compounds as electron carriers between an oxidoreductase and an electrode in an electrochemical system.

Compared to colorimetric methods for the determination of an analyte in a liquid which are evaluated visually or photometrically, a corresponding electrochemical determination offers the advantage that the electrochemical reaction yields current directly which can be converted into a concentration. In contrast the path in colorimetric methods is indirect via a battery →current→light→residual light (remission or transmission)→current→measured value.

For electrochemical methods of determination it is necessary to oxidize the analyte to be determined or to convert it into a substance which can be oxidized by means of chemical or enzymatic methods. The direct electrochemical oxidation of an analyte or of a substance derived therefrom at the surface of an electrode requires high overvoltages i.e. potentials. This method is very unselective. Many other substances which can also be in the sample to be examined are also oxidized in this process. Such a method can therefore hardly be used analytically.

Thus, the oxidizable analyte or the oxidizable substance derived from the analyte is usually reacted with a corresponding oxidoreductase and a reducible substance whose reduced form can be reoxidized at the electrode.

In this case the oxidizable analyte or theoxidizable substance derived from the analyte is selectively oxidized by the enzyme. The enzyme reduced in this way is oxidized by the reducible substance which is present and the reduced reducible substance is oxidized at the electrode. The reducible substance thus serves as a carrier of electrons from the enzyme onto the electrode. It is therefore a prerequisite that the reducible substance is so chosen that it is converted rapidly and specifically by the enzyme and by the electrode.

In "Theory and applications of enzyme electrodes in analytical and clinical chemistry", Publisher Wiley, New York (1980), pages 197–310, P. W. Carr et al describe the reaction of glucose with oxygen as the reducible substance catalysed enzymatically by glucose oxidase and detection of the hydrogen peroxide formed at an electrode. Disadvantages of this method are side reactions of the hydrogen peroxide which is itself a strong oxidizing agent and side reactions at the electrode surface as a result of the high positive potential used. This method therefore requires special prior separations to exclude interfering components in the samples to be examined. A further disadvantage is the oxygen requirement. The oxygen diffusion from air into the sample, and within the sample, becomes rate determining especially at high glucose concentrations and may thus in certain circumstances falsify the results of the method.

A sensor electrode system for the determination of a component of a mixture of substances is described in EP-A-0 125 137 which has at least two electrically conductive agents which are each present isolated from one another and which can be brought into electrical contact with the sample to be examined by means of an electrically conductive surface whereby one of the electrically conductive surfaces contacts an oxidoreductase and a so-called "mediator compound" which transfers electrons between this enzyme and the electrically conductive surface. An organometallic substance is used as the mediator compound which has at least two organic rings of which each has at least two conjugated double bonds and in which a metal atom shares its electrons with each of these rings. Ferrocene or ferrocene derivatives are used, just as in EP-A-0 078 636, as preferred mediator compounds. In this connection, it should be taken into account that such compounds must first be oxidized, for example to a ferrocinium ion, before they are ready to accept electrons from the oxidoreductase. This leads to so-called "starting currents" which already occur in the absence of an analyte which of course interferes with an amperometic method in which the resulting current is a measure for the amount of the analyte to be determined. In addition, the sparing solubility of such metalloorganic compounds is disadvantageous since this leads to an oxygen preference for example when oxidases such as glucose oxidase are used as the oxidoreductase and this therefore leads to a current which is only small and to an oxygen dependence especially at low enzyme substrate concentrations. When using these electron carriers in a reduced form, a sparing solubility and/or the use of low concentrations are necessary in order to obtain starting currents which are just acceptable.

Electron carriers for electrochemical methods of determination which are well-known from the state of the art are in general characterized in that they are reduced in the presence of the analyte to be determined by an oxidoreductase and are reoxidized to the initial compound at an electrode. If the concentration of the reducible substance functioning as the electron carrier is substantially smaller than the concentration of the analyte to be determined then only kinetic methods can be carried out. For end-point determinations it is necessary that the reducible substance functioning as the electron carrier is present dissolved in an excess compared to the analyte to be determined in order that the analyte to be determined is completely reacted. In this process an amount of reducible substance is reacted which is proportional to the analyte to be determined. Advantages over the kinetic measurement are in particular the extended range of linearity of the current/concentration relation in amperometric methods and the improved competitiveness of the more highly concentrated reducible substance compared to oxygen when using oxidases as oxidoreductases. However, a disadvantage is that, for a complete reaction, it is necessary to use a reducible substance, i.e. an oxidizing agent, as the electron carrier with a potential which is substantially higher than that of the enzyme substrate and that, in the electrochemical determination, it is in addition necessary to use an excess of oxidizing agent which even further increases the necessary potential. However, high working potentials favour unspecific electrode reactions in particular when samples have to be investigated which contain a multitude of components in addition to the analyte to be determined.

In this respect there are still no satisfactory solutions for the electrochemical determination of an analyte via an enzymatic redox reaction. There is a lack of reducible substances functioning as electron carriers which can be applied universally, which react rapidly with oxidoreductases and which exhibit an uninhibited reaction at electrode surfaces at low potential.

The object of the present invention was to solve this problem. In particular reducible substances should be found which can function as electron carriers between an oxidoreductase and an electrode in an electrochemical system. This object is achieved by the invention characterized by the patent claims.

The invention provides a method for the electrochemical determination of an analyte in the presence of an oxidoreductase and a reducible substance which transfers electrons which arise during the course of the determination reaction from the oxidoreductase onto an electrode and thus leads to a signal which is a measure for the analyte to be determined whereby the reducible substance is enzymatically reduced and oxidized at the electrode which is characterized in that the substance which forms at the electrode by oxidation is different from the reducible substance used initially.

The invention also provides a method for the electrochemical determination of an oxidoreductase in the presence of a corresponding enzyme substrate and a reducible substance which is capable of transferring electrons from the oxidoreductase onto an electrode and thus leads to a signal which is a measure for the enzyme to be determined whereby the reducible substance is enzymatically reduced and oxidized at the electrode which is characterized in that the substance which forms by oxidation at the electrode is different from the reducible substance used initially.

In addition, the invention provides the use of a substance, which can accept electrons from an oxidoreductase with formation of an electron-rich aromatic amine, as an electron carrier between an oxidoreductase and an electrode in an electrochemical system.

The invention also provides a sensor electrode system for the determination of an analyte in a liquid sample containing at least two electrically conductive agents which are present isolated from one another and which each can be brought into electrical contact with the sample to be examined by means of an electrically conductive surface in which at least one of the electrically conductive surfaces contacts an oxidoreductase and a reducible substance which is capable of transferring electrons between the oxidoreductase and the electrically conductive surface which is characterized in that a compound is used as the reducible substance which, after reduction by the oxidoreductase, is oxidized at the electrically conductive surface to a substance which is different from the reducible substance used initially.

Moreover, the invention provides a sensor electrode system for the electrochemical determination of an oxidoreductase in a liquid sample containing at least two electrically conductive agents which are present isolated from one another and which each can be brought into electrical contact with the sample to be examined by means of an electrically conductive surface in which at least one of the electrically conductive surfaces contacts an oxidoreductase substrate and a reducible substance which is capable of transferring electrons between the oxidoreductase and the electrically conductive surface which is characterized in that a compound is used as the reducible substance which, after reduction by the oxidoreductase, is oxidized at the electrically conductive surface to a substance which is different from the reducible substance used initially.

Finally the invention provides the use of a substance which can accept electrons from an oxidoreductase with formation of an electron-rich aromatic amine for the production of a sensor electrode system according to the present invention.

It has turned out that the disadvantages of the known prior-art methods for the electrochemical determination of an analyte in the presence of an oxidoreductase and a reducible substance which are caused by the high potential which is necessary, in particular when using an excess of the reducible substance functioning as the electron carrier over the analyte to be determined, can be in the main avoided by a non-reversible reaction. Since an oxidized substance is formed at the electrode which is different from that used initially as the reducible substance, the electrochemical determination can be carried out at a particularly low potential and thus without risk of interfering reactions. The advantage of this low potential can then also be utilized when the reducible substance functioning as the electron carrier is only used in a small amount compared to the analyte to be determined, namely when the reducible substance used initially as well as the substance formed by oxidation at the electrode are reduced by the oxidoreductase which is necessary for the electrochemical method. If the reducible substance used initially as well as the substance formed by oxidation at the electrode are reduced by the oxidoreductase to the same substance, then the reducible substance used initially acts as a storage form for the second reducible substance which is recycled between the electrode and enzyme and which is different from the reducible substance used initially.

The advantages of the method according to the present invention are a consequence of the fact that substances can be selected as reducible substances from which a compound is formed by enzymatic reduction which can be oxidized at low voltage at the electrode. During the oxidation at the electrode there is still only a negligible concentration of this newly oxidized substance present. Hitherto, the enzymatically reduced compound had to be oxidized at the electrode back to the reducible substance used initially which was already present in a high concentration. An increased positive potential was necessary for this.

Compounds which can be used advantageously as reducible substances in the sense of the invention are those which, during oxidation of a suitable substrate for the oxidoreductase used, accept electrons which arise from the enzyme and form an electron-rich aromatic amine in this process. In this connection an electron-rich aromatic amine is understood as a compound which is richer in electrons than aniline and which because of its richness in electrons can be oxidized at the electrode at a low potential. For example all those aniline derivatives come into consideration which carry one or several $+I$ or/and $+M$ substituents such as hydroxy, alkyl, alkoxy, aryloxy, alkylthio, arylthio, amino, mono-alkylamino and dialkylamino residues on the aromatic ring or on the aniline nitrogen.

Alkyl, alkoxy, alkylthio, mono-alkylamino and dialkylamino residues are residues in which alkyl represents a hydrocarbon residue with 1 to 6 carbon atoms which itself can be substituted by a hydroxy group, an amino group which is substituted, if desired, once or several-fold by alkyl with 1 to 6 carbon atoms, $PO_3H_2$, $SO_3H$ or $CO_2H$. The acid residues $PO_3H_2$, $SO_3H$ and $CO_2H$ can be present as such or in a salt form as ammonium, alkaline or alkaline-earth salts.

Aryloxy and arylthio residues are aromatic residues with 6 to 10 carbon atoms in which phenoxy and phenylthio residues are particularly preferred.

Ammonium salts are those which contain the ammonium ion $NH_4^+$ or those which contain ammonium cations which are substituted once or several-fold by alkyl, aryl or aralkyl residues. Alkyl in alkyl and aralkyl residues denotes a hydrocarbon residue with 1 to 6 carbon atoms. Aryl in aryl and aralkyl residues is an aromatic ring system having 6 to 10 carbon atoms in which phenyl is preferred. A preferred aralkyl residue is benzyl.

Alkaline salts are preferably those of lithium, sodium or potassium. Alkaline-earth salts are preferably those of magnesium or calcium.

Aniline derivatives are also understood to include compounds which carry an unsubstituted amino group or an amino group substituted once or several-fold by $+I$ or/and $+M$ substituents, such as for example alkyl, on an aromatic ring system which is anellated with one or several aromatic or/and alicyclic rings. In this connection hydrocarbon-aromatic systems as well as heteroaromatics come into consideration as aromatic rings. Examples are anellated benzene or naphthaline rings or an anellated pyridine ring.

Alicyclic rings are understood as saturated or unsaturated cycloaliphatics with 5 to 7 carbon atoms, preferably 5 or 6 carbon atoms.

Possible alkyl substituents of the amino group can be hydrocarbon residues with 1 to 6 carbon atoms which can themselves be substituted by a hydroxy group, an amino group substituted, if desired, once or several-fold by alkyl with 1 to 6 carbon atoms, $PO_3H_2$, $SO_3H$ and $CO_2H$. The acid residues $PO_3H_2$, $SO_3H$ and $CO_2H$ can be present as such or in a salt form as ammonium, alkaline or alkaline-earth salts for which the definition given above also applies.

The examples of $+I$ or/and $+M$ substituents given above is not to be considered to be complete. Those skilled in the art will know whether a given substituent is a $+I$ or/and $+M$ substituent and all these substituents shall be understood as possible substituents in the electron-rich aromatic amines as useful according to the present invention.

Particularly preferred as reducible substances which, when accepting electrons from the oxidoreductase, lead to an electron-rich aromatic amine that can then be oxidized at an electrode at low potential are compounds from the group of compounds of the general formula I

X—R    (I)

in which
R represents an electron-rich aromatic residue and
X represents NO or NHOH,
and compounds of the general formula II

HO—N=Y    (II)

in which
Y represents a quinoid system which can, after reduction, be denoted electron-rich in the aromatic state.

In this connection an electron-rich aromatic residue is understood as the alternatives listed above for electron-rich aromatic amines.

Such reducible substances according to the present invention are reduced to aromatic amines when accepting electrons from oxidoreductases and are not oxidized to the initial reducible substances on oxidation at an electrode. As is well known to one skilled in the art, electrons are removed from the aryl residue during the electrochemical oxidation of electron-rich aromatic amines resulting in radicals or quinoid systems. However, quinoid oximes, hydroxylamines and nitroso compounds do not form.

The electrochemically oxidized compounds can often again accept electrons themselves from oxidoreductases and are in this way reduced back to electron-rich aromatic amines. It is therefore also possible to use reducible substances according to the present invention in a low concentration when comoared with the analyte to be determined. In this way they act as a storage form for the electron-rich aromatic amines which are formed when electrons are accepted from the oxidoreductase and can be recycled as electron carriers between the oxidoreductase and electrode.

Outstanding examples of electron carriers according to the present invention have proven to be
N-(2-hydroxyethyl)-N'-p-nitrosophenyl-piperazine,
N,N-bis-(2-hydroxyethyl)-p-nitrosoaniline,
o-methoxy-[N,N-bis-(2-hydroxyethyl)]-p-nitrosoaniline,
p-hydroxynitrosobenzene,
N-methyl-N'-(4-nitrosophenyl)-piperazine,
p-quinone dioxime,
N,N-dimethyl-p-nitrosoaniline,
N,N-diethyl-p-nitrosoaniline,
N-(4-nitrosophenyl)-morpholine,
N-benzyl-N-(5'-carboxypentyl)-p-nitrosoaniline,
N,N-dimethyl-4-nitroso-1-naphthylamine,
N,N,3-trimethyl-4-nitrosoaniline,
N-(2-hydroxyethyl)-5-nitrosoindoline,
N,N-bis-(2-hydroxyethyl)-3-chloro-4-nitrosoaniline,
2,4-dimethoxy-nitrosobenzene,
N,N-bis-(2-methoxyethyl)-4-nitrosoaniline,
3-methoxy-4-nitrosophenol,
N-(2-hydroxyethyl)-6-nitroso-1,2,3, tetrahydroquinoline,
N,N-dimethyl-3-chloro-4-nitrosoaniline,
N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, N-(2-hydroxyethyl)-N-(2-(2-hydroxyethoxy)-ethyl)-4-nitrosoaniline.

A particularly preferred reducible substance according to the present invention is N,N-bis-(2-hydroxyethyl)-p-nitrosoaniline. N-(2-hydroxyethyl)-N-(2-(2hydroxyethoxy)-ethyl)-4-nitrosoaniline is especially preferred.

Many compounds of the general formula I which can be used according to the present invention are well-known. Nitrosoaniline derivatives of the general formula III are new

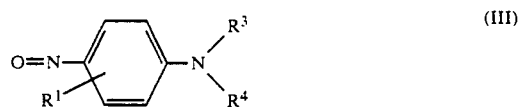

in which
R¹ denotes hydrogen, halogen, alkoxy or alkylthio,
R² represents an alkyl residue and
R³ represents an hydroxyalkyl residue or
R² and R³ are the same or different and each represents a dialkylaminoalkyl residue, an hydroxyalkoxyalkyl or alkoxyalkyl residue substituted, if desired, by OH in the alkyl moiety or a polyalkoxyalkyl residue which is substituted, if desired, by an hydroxy residue in the alkyl moiety or
R² and R³ form an alkylene residue interrupted by sulphur or nitrogen in which nitrogen is substituted by an alkyl, hydroxyalkyl, hydroxyalkoxyalkyl, alkoxyhydroxyalkyl, dioxanylyl-alkyl or polyalkoxyalkyl residue each of which is itself substituted, if desired, in the alkyl moiety by a hydroxy residue or
if R¹ is in the ortho position to NR²R³, R² also together with R¹ represents an alkylene residue whereby R³ then represents a hydroxyalkyl residue or, if the alkylene residue contains 3 carbon atoms, it also represents, if desired, an alkyl residue or if R¹ is not hydrogen, R² and R³ are the same or different and each represents an hydroxyalkyl residue or a salt of this derivative.

In this connection halogen denotes fluorine, chlorine, bromine or iodine. Fluorine and chlorine are particularly preferred. Alkyl, alkoxy or alkylthio are residues with 1-6 carbon atoms, those with 1-3 carbon atoms are particularly preferred. The foregoing definition for alkyl also applies to the alkyl moiety in hydroxyalkyl, dialkylaminoalkyl, hydroxyalkoxy-alkyl, alkoxyalkyl, polyalkoxyalkyl, alkoxy-hydroxyalkyl and dioxanylyl-alkyl residues.

A dioxanylyl-alkyl residue is a residue in which a dioxan ring system is bound to an alkyl residue. It is preferably a 1,4-dioxan ring system, i.e.

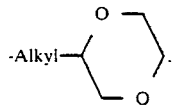

A polyalkoxyalkyl residue is an -alkyl-(alkoxy)$_n$-alkoxy residue in which n=1-10. It is preferred that n=1-4. It is particularly preferred that n=1-3. An alkylene residue is a straight-chained or branched, —preferably straight-chained-,saturated or unsaturated, —preferably saturated-,hydrocarbon chain consisting of 2-5, preferably 2-4 C-atoms with two free binding sites. Within the meaning of an alkylene residue of R² and R³ which is interrupted by sulphur or nitrogen, a thiomorpholine or piperazine residue formed by the inclusion of the nitrogen atom of the general formula III is preferred. The piperazine residue is especially preferred.

Within the meaning of an alkylene residue formed from R¹ and R², the indoline or 1,2,3,4-tetrahydroquinoline residue formed by the inclusion of the aromatic ring of the general formula III is preferred.

As the salt of a nitrosoaniline derivative according to the present invention of the general formula III, those of strong acids, in particular mineral acids such as hydrochloric acid, sulphuric acid, nitric acid and phosphoric acid are preferred. Hydrochlorides are especially preferred, these are salts of hydrochloric acid.

The following new nitrosoaniline derivatives are especially preferred according to the present invention:
a) 2,2'-[(3-fluoro-4-nitrosophenyl)imino]bis-ethanol,
b) 2,2'-[(3-chloro-4-nitrosophenyl)imino]bis-ethanol,
c) 2,2'-[(3-methoxy-4-nitrosophenyl)imino]bis-ethanol,
d) 2,2'-[(3-methylmercapto-4-nitrosophenyl)imino]bis-ethanol,
e) 2-[(2-hydroxyethoxy)ethyl-(4-nitrosophenyl)amino]ethanol,
f) 2-[(2-methoxyethoxy)ethyl-(4-nitrosophenyl)amino]ethanol,
g) 1-[N-(2-hydroxyethyl)-(4-nitrosoanilino)]-3-methoxy-2-propanol,
h) 1-[N-(2-hydroxyethyl)-(4-nitrosoanilino)]-3-(2-hydroxyethoxy)-2-propanol,
i) 1-methyl-4-(4-nitrosophenyl)-piperazine,
j) 4-(4-nitrosophenyl)-1-piperazino-ethanol,
k) 5-nitroso-1-indoline ethanol,
l) 1-methyl-6-nitroso-1,2,3,4-tetrahydroquinoline,
m) 6-nitroso-3,4-dihydro-1(2H)quinoline ethanol and their salts.

Of these the compounds a), d), e), f), g) and h) as well as their salts are particularly preferred. Compound e) or its salts, in particular the hydrochloride, is especially preferred.

The compounds of the general formula III can be produced by reacting a compound of the general formula IV,

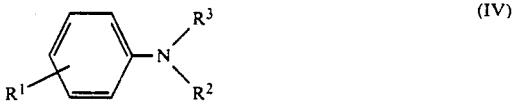

in which R¹, R² and R³ have the same meaning as in compounds of the general formula III, with nitrite. An analogous process is known from J. J. D'Amico et al., J. Amer. Chem. Soc. 81, 5957 (1959).

Alkali nitrite is preferably used as the nitrite, in which lithium, sodium, potassium, rubidium or caesium are possible as the alkali metal; sodium nitrite and potassium nitrite are preferably used. Sodium nitrite is especially preferred. The reaction preferably takes place in an acid medium at low temperature. It is advantageous when the temperature is below 10° C., preferably between −10 and +5° C.

It is advantageous when the reaction of a compound of the general formula IV with nitrite takes place in an aqueous medium. The pH should be preferably less than 3, particularly preferably less than 2.

In a preferred embodiment for the reaction, a compound of the general formula IV or a salt thereof, preferably a salt of a mineral acid such as hydrochloric acid, sulphuric acid, nitric acid or phosphoric acid, is first added to an aqueous acidic medium and cooled.

Then, nitrite, preferably in a dissolved form, is added while maintaining the reaction mixture at a low temperature. It is advantageous when an aqueous medium is also used as the solvent for the nitrite. After addition of the nitrite the reaction mixture is kept at a low temperature until the reaction is completed. In order to process the reaction mixture it is preferably extracted with an organic solvent and the product is isolated from the extract.

Compounds which can be used according to the present invention as electron carriers can be stored and used in an oxidized form. Starting currents are avoided by this means and end-point determinations can be carried out with an excess of electron carriers. Compounds which can be used according to the present invention as electron carriers are stable on storage and can react rapidly with oxidoreductases. Above all they are able to compete with oxygen when using oxidases and can be used in excess over the highest analyte concentration to be determined. It is especially the latter property which is made possible by the good solubility of the electron carriers according to the present invention in an aqueous medium.

In the electrochemical determination of analytes in body fluids a particular advantage of the compounds which can be used according to the present invention as electron carriers is their property of not being non-enzymatically reduced, or only to a negligible extent, by substances in body fluids which act reductively. The electron carriers according to the present invention are rapidly oxidized at the electrode surface and are not sensitive to oxygen in their reduced form. With these compounds a low potential can be used for the oxidation at the electrode.

In the present invention a substance to be determined is referred to as analyte. In this connection it is usually a component of a mixture of substances. The process according to the present invention offers particular advantages in this connection when determining an analyte in a body fluid such as blood, plasma, serum or urine because in this situation it is especially important that a specific reaction takes place with only one component of the biological multicomponent system.

The method according to the present invention for the electrochemical determination of an analyte is based on the fact that the analyte is itself oxidized by an oxidoreductase and therefore constitutes a corresponding enzyme substrate, or the analyte is converted in one or several previous reactions, preferably enzymatic reactions, into a compound which can be oxidized by an oxidoreductase. The electrons which arise during such an oxidation are proportional to the amount of the analyte to be determined. If these electrons are transferred onto an electrode by a reducible substance according to the present invention this then leads to a signal which is a measure for the analyte to be determined. Amperometric methods are possible in which a current is measured or potentiometry i.e. measurement of a voltage.

As oxidoreductases for the method according to the present invention are preferred oxidases, non-NAD(P)-dependent dehydrogenases or diaphorase. For example, according to the present invention glucose can be determined with glucose oxidase, lactate with lactate oxidase, glycerol phosphate by means of glycerol phosphate oxidase or cholesterol by means of cholesterol oxidase. As a non-NAD(P)-dependent dehydrogenase, glucose-dye oxidoreductase can for example be used for the determination of glucose. Diaphorase which can also be denoted NADH:dye oxidoreductase can be used advantageously for the detection of NADH.

In cases in which an analyte, which does not itself serve as a substrate for an oxidoreductase, has to be determined electrochemically, this analyte can be converted by one or several preliminary reactions, in particular enzymatic reactions, into a compound which is accepted by an oxidoreductase as substrate. For example, tryglycerides can be determined in that they are cleaved by means of an esterase into glyerol and acid residues, glycerol is converted to glycerol phosphate with glycerol kinase and ATP, and this is finally oxidized by means of glycerol phosphate oxidase; the electrons which are produced in this latter step are transferred by an electron carrier according to the present invention to an electrode whereby a current is produced which is proportional to the amount of triglycerides in the sample to be determined.

Total cholesterol can also for example be determined in an analogous manner by cleaving cholesterol esters with cholesterol esterase and the cholesterol formed in this manner is determined by means of cholesterol oxidase. Also in this case the amount of cholesterol formed thus and the electrons released in the oxidation by means of cholesterol oxidase, which are transferred onto an electrode by means of a reducible substance according to the present invention and thus produce a current, are proportional to the amount of total cholesterol to be determined.

The enzyme diaphorase may be used for the determination of NADH. Electrons from diaphorase can also be transferred onto an electrode by means of reducible substances according to the present invention. Since very many biological substances can be reacted enzymatically with formation of NADH, it is possible in this way to convert many analytes into NADH by enzymatic reaction sequences and then finally to determine this at an electrode by means of diaphorase and a reducible substance used according to the present invention.

From the aforementioned it goes without saying that according to the present invention oxidoreductases can of course also be determined if a corresponding compound which is accepted as the enzyme substrate and a reducible substance according to the present invention are employed. Thus, for example glucose oxidase can be determined electrochemically if glucose and an electron carrier according to the present invention are contacted with the sample to be determined in the presence of a corresponding sensor electrode system.

A special feature of the method according to the present invention is that the reducible substance used to transfer electrons from an oxidoreductase onto an electrode is stable on storage in its oxidized form and in addition is readily water soluble which is particularly important for the determination of analytes in body fluids such as blood, plasma, serum and urine. The reducible substances capable of being used according to the present invention react rapidly with oxidoreductases and are capable of competing very well with oxygen, in particular in reactions with oxidases. Because of their solubility they can be used very well for amperometric end-point methods in which an excess is required over the highest analyte concentration to be determined. Since the reducible substances capable of being used according to the present invention are reduced non-enzymatically only to a negligible extent in body fluids by reducing agents which are present there, are oxidized rapidly at the electrode surface and are hardly oxygen sensitive in their reduced form, these substances are very well suited to the specific, interference-free electrochemical determination of analytes. Moreover, the specific electrochemical determination of analytes without interference is above all a consequence of the fact that the reducible substances capable of being used according to the present invention only require a small electrode potential.

The method according to the present invention for the electrochemical determination of an analyte is not limited to particular electrochemical devices. For example state-of-the-art sensor electrode systems may be used for this. In principle for the determination of an analyte in a liquid sample those sensor electrode systems are suitable which contain at least two electrically conductive agents as electrodes which are present isolated from one another and which each can be brought into electrical contact with the sample to be determined by means of an electrically conductive surface. In this connection it is conceivable that only two electrodes, namely a working electrode and a reference electrode are used. A measuring arrangement without a reference electrode i.e. with only a working electrode and counterelectrode is also possible. In this the voltage is merely kept constant externally. The use of three electrodes is also possible, namely a reference electrode, a working electrode and a counterelectrode. Corresponding sensor electrode systems are known from the state of the art, for example from G. Henze and R. Neeb, "Elektrochemische Analytik", Springer-Verlag (1986).

It is important for the electrochemical determination of an analyte that (at least) one electrode, i.e. an electrically conductive surface, contacts an oxidoreductase and a reducible substance which is capable of transferring electrons between the oxidoreductase and the electrically conductive surface. In this connection, it is conceivable that all the required reagents are in a solution together with the sample to be examined or that a portion of the reagents, preferably the oxidoreductase and/or the reducible substance which tranfers the electrons, are immobilized on an electrode and the remainder are present in solution, or that all of the reagents necessary for the determination are immobilized on an electrode. In principle is is not decisive for the function of a sensor electrode system whether the working electrode contacts the oxidoreductase and the reducible substance which functions as the electron carrier as dissolved substances or whether these substances are applied to the electrode as solid substances and which, if desired, dissolve on contact with the liquid sample to be determined or even remain immobilized on the electrode after contact with the liquid sample to be determined.

It goes without saying that the previous description applies analogously to the determination of an oxidoreductase. It must then be taken into account that the sensor electrode system contacts an oxidoreductase substrate and a reducible substance according to the present invention. Apart from this the statements made for the determination of an analyte apply correspondingly in this case.

The attached figures elucidate the invention further. They show

FIG. 1 in part a) A scheme of the function of the reducible substances capable of being used according to the present invention in methods according to the present invention and sensor electrode systems when the concentration of the electron carrier is larger than or the same as the analyte concentration to be determined.

FIG. 1 in part b) A scheme of the function of substances carrying electrons in state-of-the-art methods and state-of-the-art sensor electrode systems.

FIG. 2 in part a) A scheme of the function of the reducible substances capable of being used according to the present invention in methods according to the present invention and sensor electrode systems when the concentration of the substance which transfers electrons is very much smaller than the concentration of the analyte to be determined.

FIG. 2 in part b) A scheme of the function of substances which transfer electrons in state-of-the-art methods and state-of-the-art sensor electrode systems.

Figure 3:
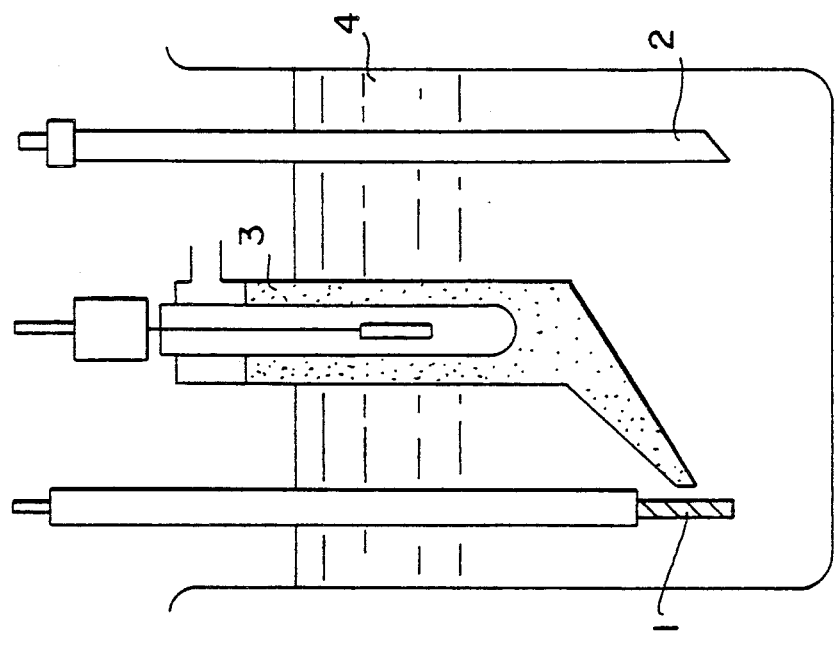

FIG. 3: A sensor electrode system for carrying out the method according to the present invention in which the required substances are present in solution.

Figure 4:
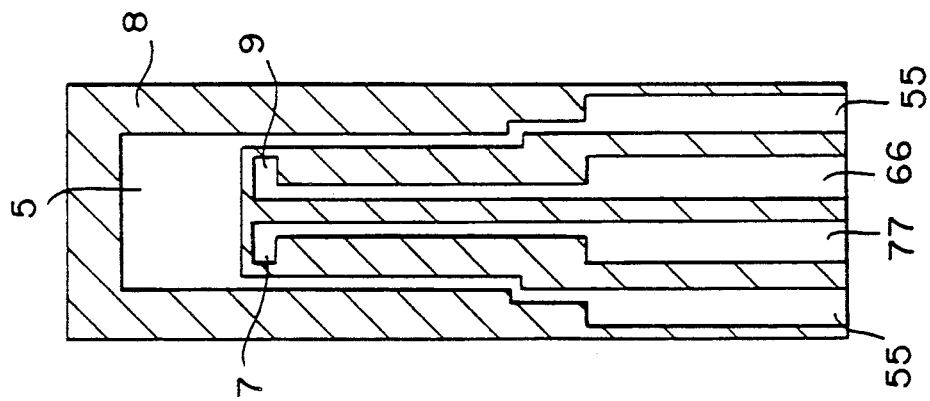

FIG. 4: A sensor electrode system for carrying out the method according to the present invention which is designed as a disposable sensor.

FIG. 5: A diagram of values obtained from cyclovoltammograms for anodic current density maxima at different glucose concentrations using N,N-bis-(2-hydroxyethyl)-p-nitrosoaniline as the substance transferring electrons in an electrochemical glucose test according to the present invention.

FIG. 6: Diagram showing the relationship between current density and NADH concentration in a NADH test according to the present invention.

Figure 7:
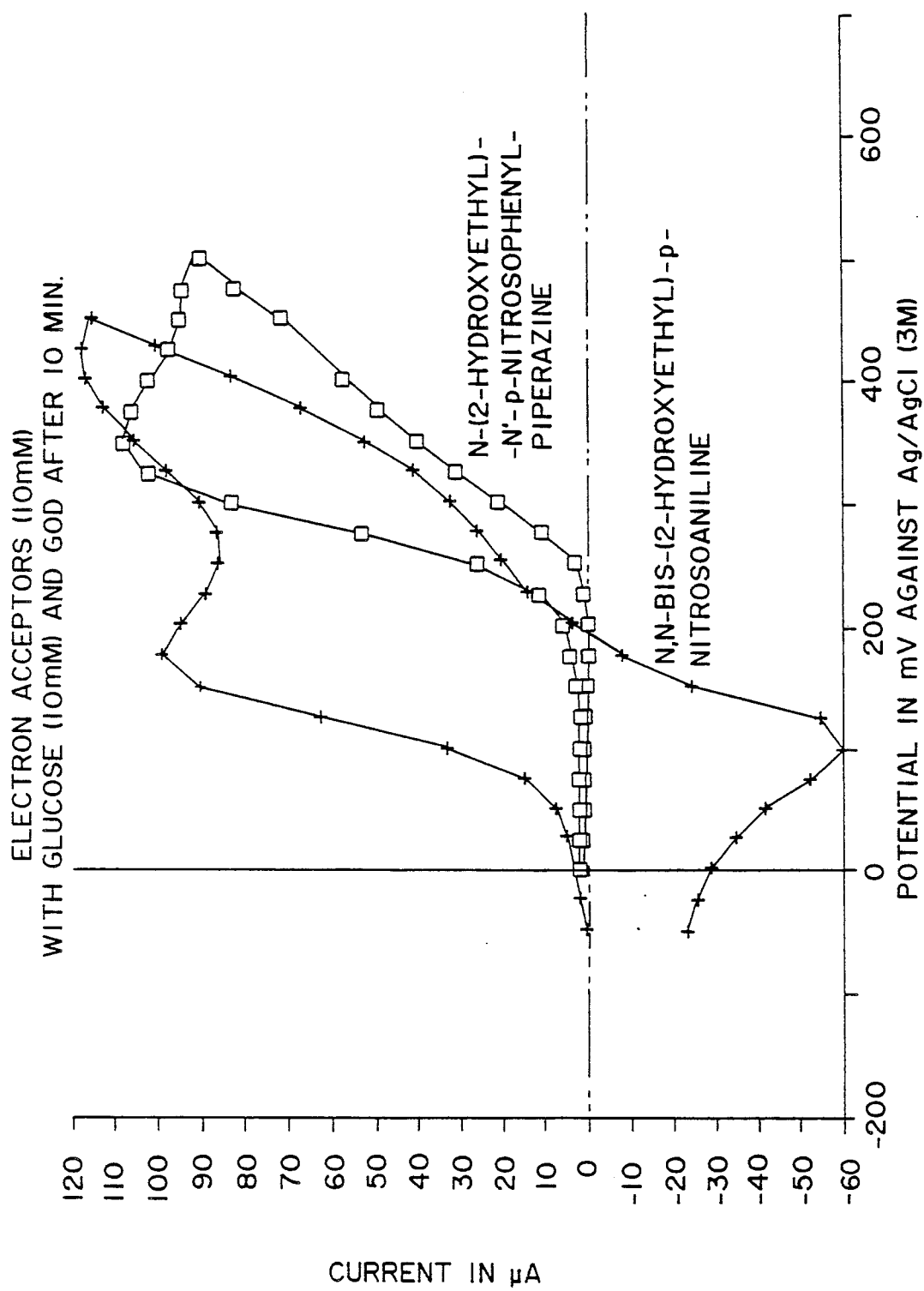

FIG. 7: Cyclovoltammograms for N-(2-hydroxyethyl)-N'-p-nitrosophenyl-piperazine and N,N-bis-(2-hydroxyethyl)-p-nitrosoaniline.

Figure 8:
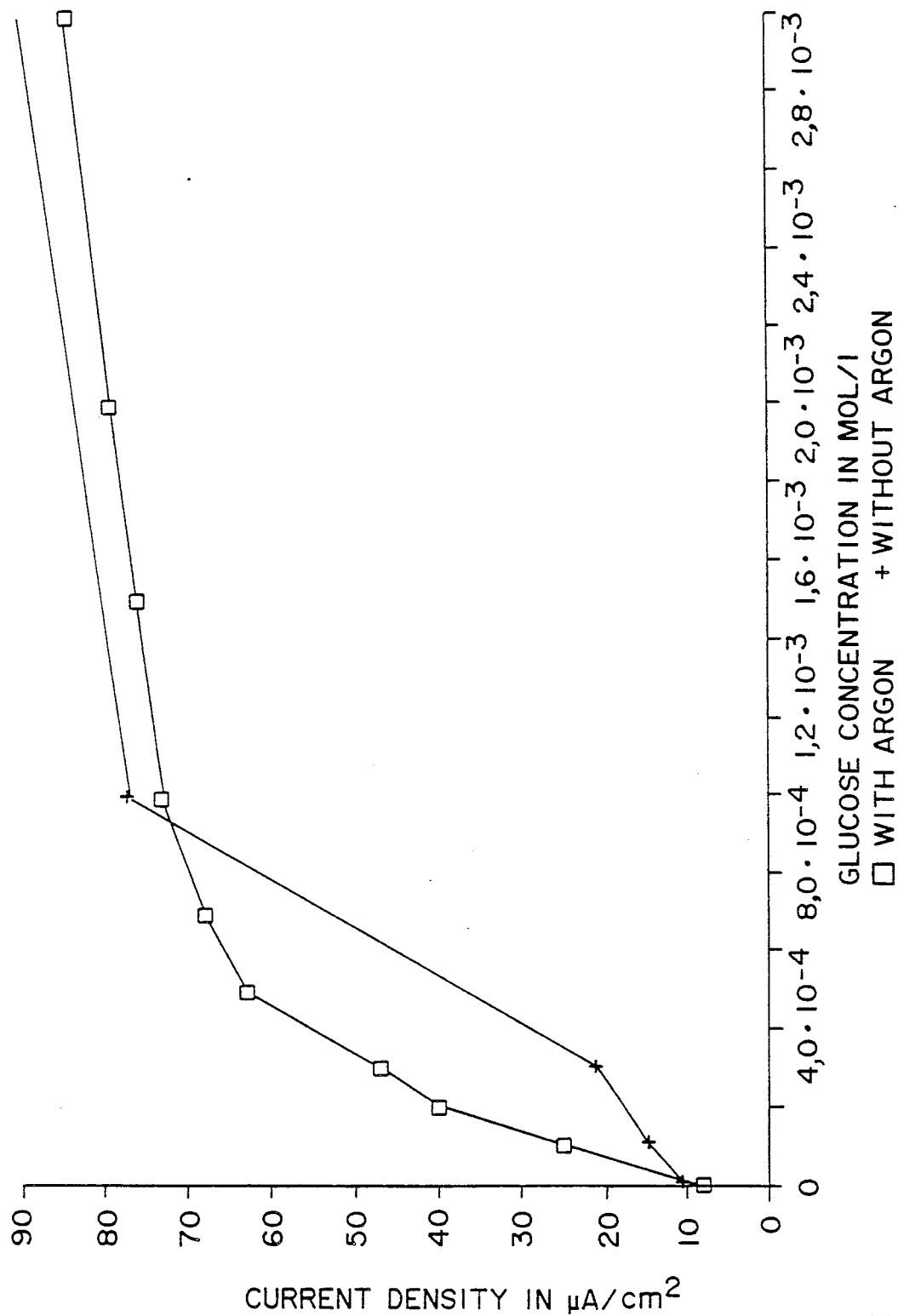

FIG. 8: Diagram of the dependence of the current density on the glucose concentration according to the method according to the present invention with N-methyl-N'-(4-nitrosophenyl)-piperazine as the substance transferring electrons in the presence and absence of atmospheric oxygen.

Figure 9:
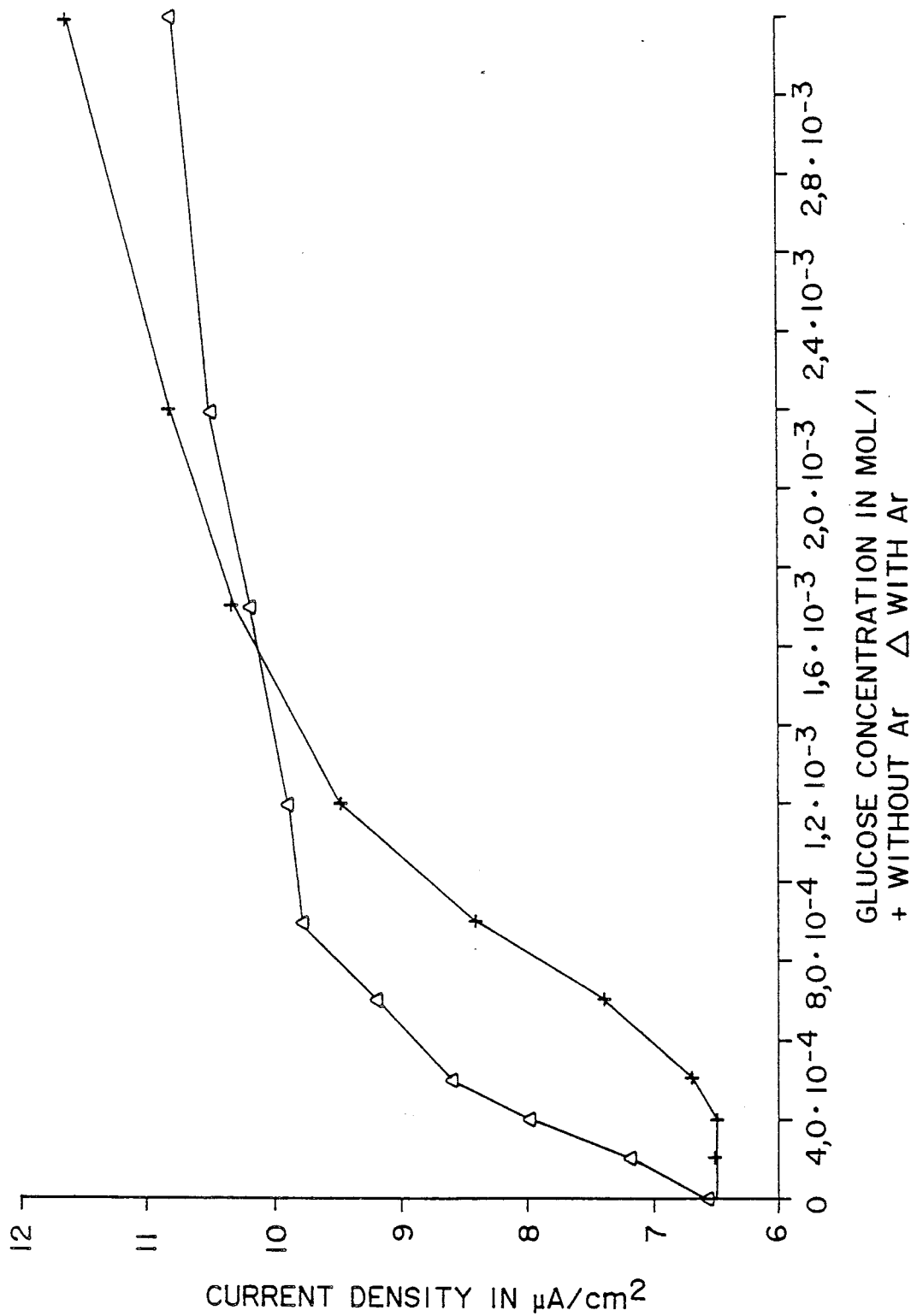

FIG. 9: Diagram of the dependence of the current density on the glucose concentration according to state-of-the-art methods with tetrathiafulvalene as the substance transferring electrons in the presence and absence of atmospheric oxygen.

Figure 10:
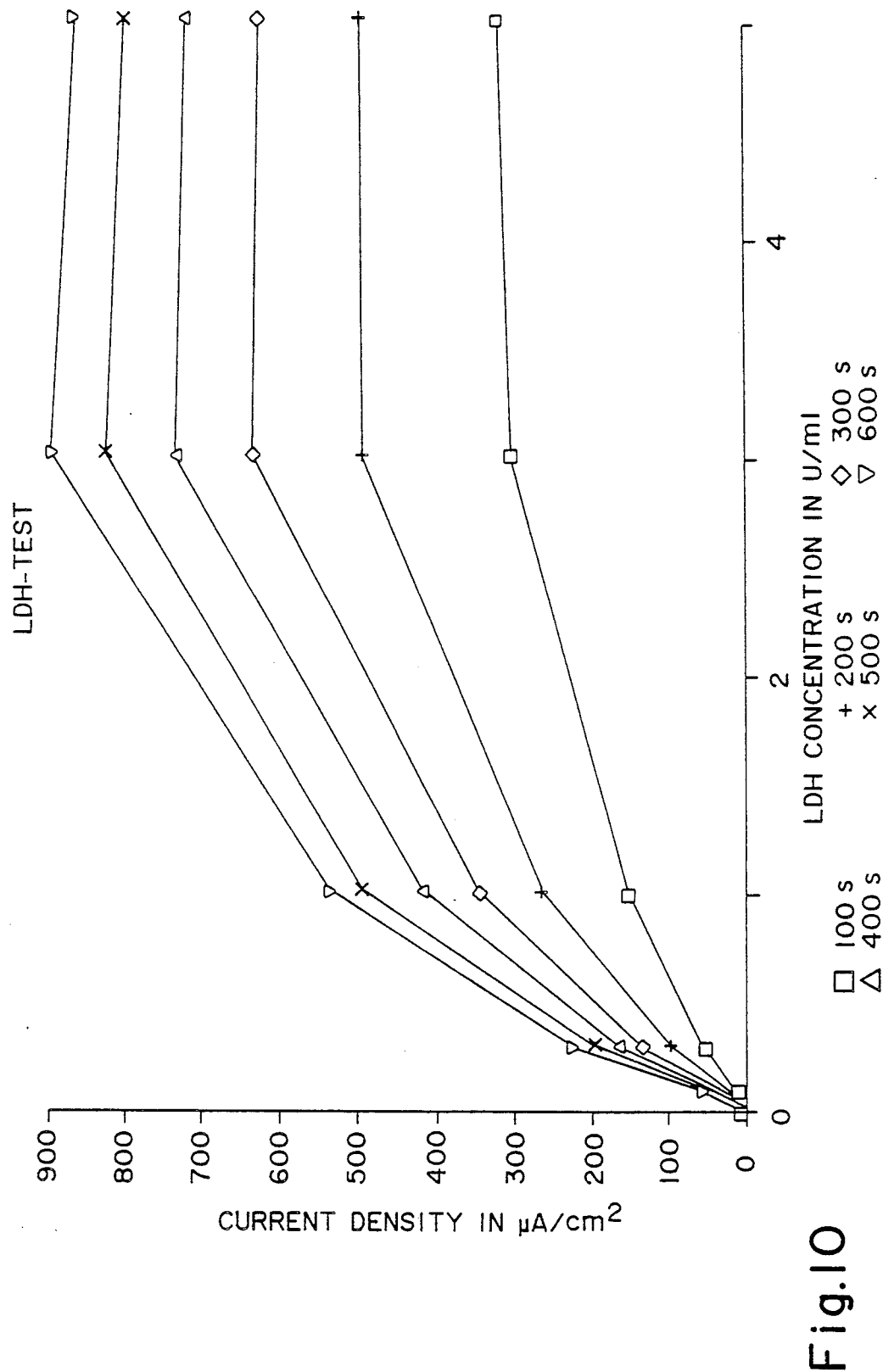

FIG. 10: Diagram of the dependence of the current density on the LDH concentration according to a method according to the present invention with N,N-bis-(2hydroxyethyl)-p-nitrosoaniline as the substance transferring electrons at different times after starting the determination reaction with lactate dehydrogenase.

Figure 11:
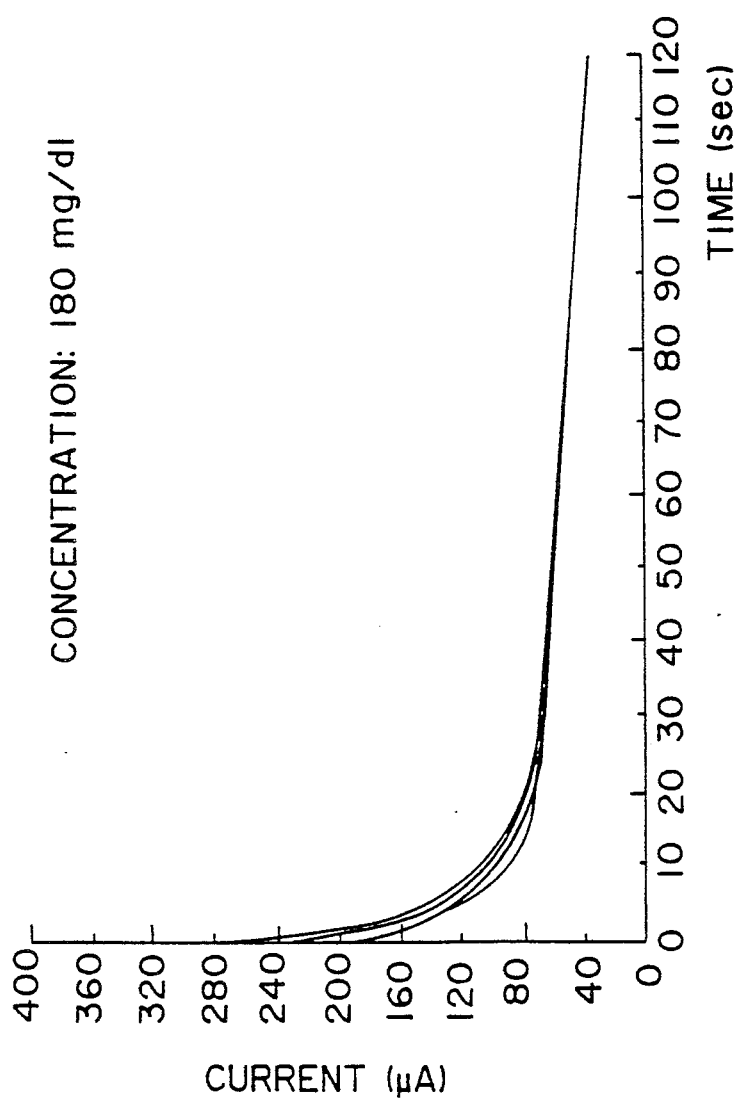

FIG. 11: Current-time curves for the method according to the present invention with a disposable electrode according to FIG. 4 for the detection of glucose.

Figure 12:
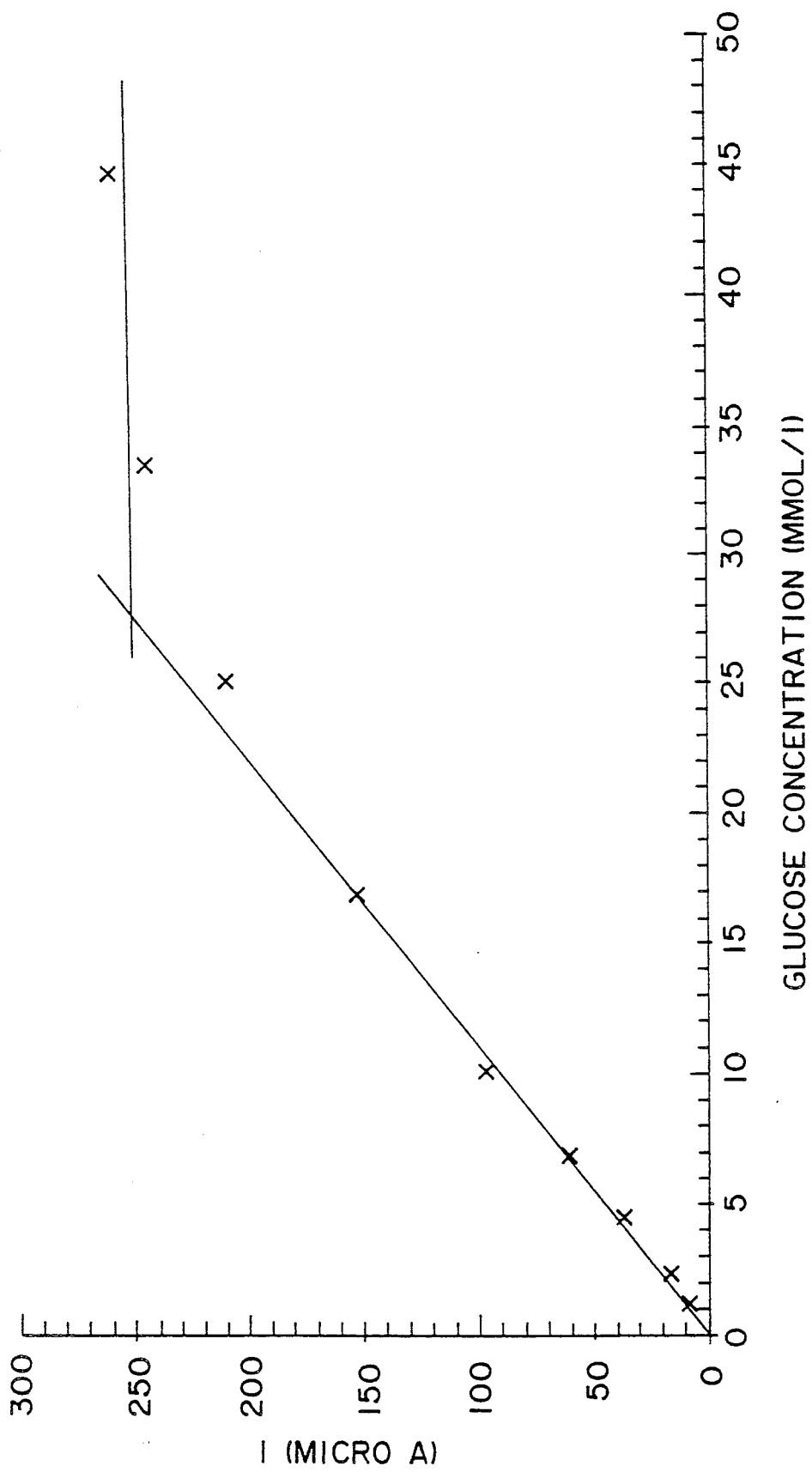

FIG. 12: Diagram of the dependence of the current on the glucose concentration according to the method according to the present invention with a disposable electrode according to FIG. 4 after 10 seconds reaction time.

In FIG. 1 and 2 the differences between the method according to the present invention (a) and the state-of-the-art method (b) are shown when using an excess of the substance which transfers electrons over the analyte to be determined (FIG. 1) and when using a very small amount of the substance which transfers electrons compared to the analyte concentration (FIG. 2). According to the state-of-the-art method according to FIG. 1b) the substance transferring electrons ($E_{ox\,1}$) is converted into the reduced form ($E_{red}$) in the presence of the analyte to be determined or of a substance derived from the analyte ($S_{red}$) which is enzymatically oxidized to ($S_{ox}$). The reduced electron carrier ($E_{red}$) is oxidized at an electrode back to the reducible substance used initially ($E_{ox\,1}$) by releasing electrons.

Figure 1A:
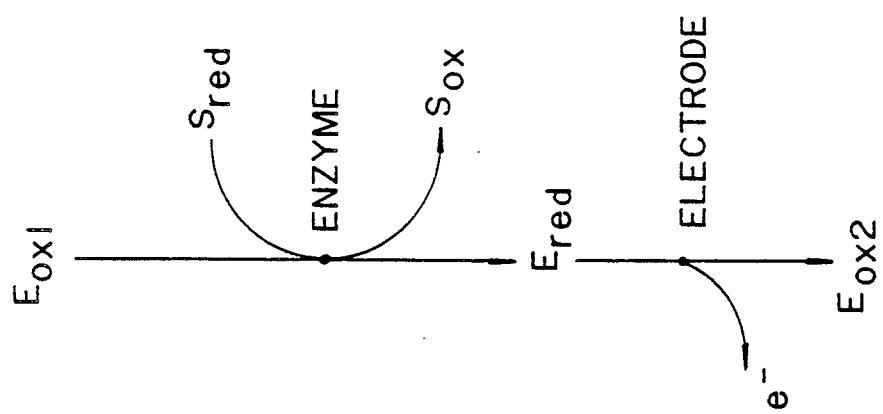

In contrast, according to the method according to the present invention in accordance with FIG. 1a), the reducible substance functioning as the electron carrier ($E_{ox\,1}$) is converted into the reduced form ($E_{red}$) in the enzymatic oxidation of the analyte to be determined, or of a substance derived from the analyte ($S_{red}$), to ($S_{ox}$). In the anodic oxidation at an electrode, an oxidized form of the electron carrier ($E_{ox\,2}$) is then formed which is different from the reducible substance used initially ($E_{ox\,1}$). As a result of the complete absence of $E_{ox\,2}$ at the start of the electrochemical oxidation, $E_{red}$ can be oxidized at a particularly low potential. The reducible substance transferring electrons according to the present invention ($E_{ox\,1}$) can be so chosen that a relatively low potential is sufficient for the anodic oxidation of the reduced form which is formed enzymatically ($E_{red}$). Interfering accompanying reactions can be avoided by this means which occur when accompanying substances in the samples to be examined are oxidized when higher potentials are applied to the electrodes and thus lead to a current flow and consequently to a false-positive result. In the state-of-the-art method according to FIG. 1b) a higher potential than that of the reducible substance used initially ($E_{ox\,1}$) is necessary, because of the excess of $E_{ox\,1}$, to reoxidize the reduced form of the electron carrier formed enzymatically ($E_{red}$).

If the reducible substance functioning as the electron carrier ($E_{ox\,1}$) is in an amount which is less than the analyte to be determined or a substance derived from the analyte to be determined ($S_{red}$), then according to the state-of-the-art method (FIG. 2b) the reducible substance can be recycled between the electrode and enzyme since the reduced form ($E_{red}$) is anodically oxidized back into the reducible substance used initially ($E_{ox\,1}$).

According to the method according to the present invention (FIG. 2a), if the oxidized form of the electron carrier formed at the electrode ($E_{ox\,2}$) is reduced by the reduced enzyme as well as the reducible substance used initially ($E_{ox\,1}$), then ($E_{ox\,1}$) can serve for example as a stable storage form for the electron carrier system $E_{ox\,2}/E_{red}$.

In principle all those sensor electrode systems can be used for the method according to the present invention which are also suitable for carrying out the state-of-the-art methods. Thus, a sensor electrode system according to FIG. 3 can be used such as that which is known from G. Henze and R. Neeb, "Electrochemische Analytik", Springer Verlag (1986).

In this system a working electrode (1), a counterelectrode (2) and a reference electrode (3) are immersed in the liquid sample to be determined (4). The usual materials can be used for the electrodes. The working electrodes and counterelectrode (1, 2) can for example advantageously consist of noble metals or such metals are used for producing the electrodes. Preferred materials for the working electrode and counterelectrodes (1, 2) are for example gold and platinum. The reference electrode (3) can also be constructed from conventional systems for this. The silver/silver chloride system is for example preferred. The reference electrode (3) is advantageouly connected via a salt bridge, for example a potassium chloride solution, with the remaining electrode system (1, 2) in the liquid sample to be determined (4).

The oxidoreductase or the oxidoreductase system (depending on whether an analyte or an oxidoreductase is to be determined) for the method according to the present invention and the reducible substance functioning as the electron carrier can be dissolved in the sample to be determined (4) or they can all, or partially, be located on the working electrode (1). The manner in which the electrodes are electrically connected to one another depends on the electrical signal to be measured and the way they have to be controlled and is obvious for one skilled in the art.

The construction of a disposable electrode which can for example be used for the detection of glucose is shown in FIG. 4. The required electrodes and their accompanying leads are mounted on an insulated carrier material (8), for example a polycarbonate foil. Suitable methods can, for example, be screen printing methods, ink jet methods, evaporation coating methods or thin film techniques. In FIG. 4 (5) denotes the working electrode, (55) denotes the accompanying electrically conductive leads, (6) denotes a reference electrode with lead (66), and (7) denotes counterelectrode with a corresponding lead (77). Well-known electrically conductive materials can be used for the electrodes and leads. Commercial graphite printing pastes can for example be used to produce the electrically conductive leads to the electrodes. The electrodes mostly contain noble metals such as silver, gold or platinum. In the sensor electrode system according to the present invention according to FIG. 4, the working electrode contains the reagents which are necessary for carrying out the electrochemical determination of an analyte or of an oxidoreductase. For the determination of glucose, these are for example glucose oxidase, a reducible substance transferring electrons according to the present invention, a buffer substance which optimizes the pH value of the sample to be examined for the enzymatic reaction, as well as, if desired, a detergent and swelling agent in order to achieve the necessary consistency for the production of an electrode with a material which makes the mixture conductive and in order to make the mixture processable as a paste. Graphite powder can for example be added as the material which makes it conductive. The reference electrode (6) and counterelectrode (7) as well as the corresponding leads (66) and (77) can for example be produced from commercial silver conducting pastes which contain pulverized silver chloride. A sensor electrode system according to FIG. 4 can be produced in a size of about 10×30 mm. The solution to be examined can be applied to the electrode surfaces or the test carrier can be immersed in the liquid to be examined in such a way that the electrode surfaces are covered with liquid. In the amperometric measurement a potential can then be applied to the electrodes and a current measured which is proportional to the analyte to be determined.

For this the current between the counterelectrode (7) and working electrode (5) is measured and regulated in such a way that a pre-determined voltage is maintained between the reference electrode (6) and working electrode (5). The measurement of the voltage between the working electrode (5) and reference electrode (6) is carried out at zero current in order that resistances of the leads do not matter. If the demands on the accuracy of the electrode potentials are very low, then the voltage measurements at zero current can be dispensed with or the reference electrode (6) can be operated simultaneously as a counterelectrode (7).

The invention is elucidated further by examples in the following.

EXAMPLE 1

Glucose Test

A sensor electrode system according to FIG. 3 is used. The working electrode (1) consists of a gold wire with an area of 0.1 cm². The counterelectrode (2) is a platinum wire with an area of 0.1 cm² and the reference electrode (3) is a silver/silver chloride system from the Orion Research Inc. Company (Boston, Mass., USA).

A solution of
0.1 mol/l potassium phosphate buffer and 0.1 mol/l potassium chloride, pH 7.0;
10 mmol/l N,N-bis-(2-hydroxyethyl)-p-nitrosoaniline and glucose at a concentration between 0 and 100 mmol/l
is in the reaction vessel.

The determination reaction is started by addition of glucose oxidase (EC 1.1.3.4) to the reaction mixture and subsequent mixing. Glucose oxidase is added in such an amount that the concentration in the reaction mixture is 0.5 mg/ml (125 U/mol). One minute after the addition of glucose oxidase a cyclovoltammogram is measured at a scan rate of 100 mV/s with a potentiostat (Mod. 273 EG & G, Princeton Applied Research, Princeton, N.J., USA). The currents of the first oxidation maximum are evaluated at 150 mV. The results obtained are shown in FIG. 5. Corresponding measurements 5 minutes after the addition of glucose oxidase or when oxygen is excluded (under argon) do not result in significant changes.

The result is a linear dependence of the anodic current density maximum on the glucose concentration up to glucose concentrations of about 30 mmol/l as can be seen from the diagram according to FIG. 5. At a higher glucose concentration than 30 mmol/l, the N,N-bis-(2-hydroxyethyl)-p-nitrosoaniline used as the substance which transfers electrons is completely converted to the corresponding phenylenediamine. Higher concentrations than 30 mmol/l glucose therefore do not lead to a further increase in current. Since two glucose molecules are needed to produce one molecule of phenylenediamine and only about two thirds of the total glucose are present in the β-form and are therefore available for conversion by glucose oxidase, the complete conversion which was found of 10 mmol/l electron carrier substance by 30 mmol/l glucose corresponds exactly to the theoretical stoichiometry.

Comparable results are obtained when using glucose-dye-oxidoreductase (EC 1.1.99.17) instead of glucose oxidase (EC 1.1.3.4) in 0.1 mol/l Tris buffer. 0.1 mol/l potassium chloride, pH 7.0 with addition of 1 % bovine serum albumin.

EXAMPLE 2

NADH test

The construction and measuring arrangement are as described in Example 1. The reaction vessel contains 0.1 mol/l potassium phosphate buffer, 0.1 mol/l potassium chloride, pH 7.0, 10 mmol/l N,N-bis-(2-hydroxyethyl)-p-nitrosoaniline and NADH at concentrations between 0 and 10 mmol/l.

The measurement is started by addition and mixing of diaphorase (NADH:dye-oxidoreductase) from microorganisms and mixing the enzyme with the reaction mixture. Enzyme is added in such an amount that the enzyme concentration in the reaction mixture is 0.2 mg/ml (3 U/ml). Measurement of the current density after 1 minute reaction time yields the linear current density-concentration relation shown in FIG. 6.

EXAMPLE 3

Determination of lactate

Lactate can also be determined using the same experimental construction and the same electron carrier as in Example 1. Lactate oxidase (EC 1.1.3.2) is used as the enzyme and 0.1 mol/l citrate buffer, 0.1 mol/l potassium chloride, pH 5.5 is used as the buffer.

EXAMPLE 4

Determination of glycerol phosphate

Glycerol phosphate can be determined analogously when in Example 1 the enzyme glucose oxidase is replaced by glycerophosphate oxidase (EC 1.1.3.21) and the buffer is replaced by 0.1 mol/l Tris buffer, 0.1 mol/l potassium chloride, pH 8.0.

EXAMPLE 5

Determination of cholesterol

Cholesterol can be determined analogously to Example 1, when in Example 1 glucose oxidase is replaced by cholesterol oxidase from Streptomyces (EC 1.1.3.6), the electron acceptor is replaced by 10 mmol/l N-methyl-N'-(4-nitrosophenyl)-piperazine and the buffer is replaced by 0.1 mol/l potassium phosphate buffer, 0.1 mol/l potassium chloride, pH 5.5 with 2% Triton × 100$^R$.

EXAMPLE 6

Reducible substances according to the present invention which transfer electrons The compounds mentioned in the following Table 1 are reacted at a concentration of 10 mmol/l in 0.1 mol/l potassium phosphate buffer, 0.1 mol/l potassium chloride, pH 7.0 with 50 mmol/l glucose and 0.5 mg/ml glucose oxidase (125 U/ml). In this case a measuring arrangement as described in Example 1 is used. Corresponding cyclovoltammograms yield the peak potentials in mV against a normal hydrogen electrode of the electron carrier reduced with glucose oxidase and glucose.

In Table 1 the ratio of the oxidation currents at the potential of the highest oxidation peak is listed after one and after ten minutes as a measure for the conversion rate.

TABLE 1

| Electron carrier | peak potentials[a] | conversion rate[b] |
|---|---|---|
| N-(2-hydroxyethyl)-N'-p-nitrosophenyl-piperazine | 340 | 97 |
| N,N-bis-(2-hydroxyethyl)-p-nitrosoaniline | 210 | 94 |
| o-methoxy-[N,N-bis-(2-hydroxyethyl)]-p-nitrosoaniline | 170 | 35 |
| p-nitrosophenol | 220 | 62 |
| p-quinone dioxime[c] | 250 | 35 |
| N,N-dimethyl-4-nitroso-1-naphthylamine | 175 | 25 |
| N,N,3-trimethyl-4-nitrosoaniline | 220 | 56 |
| N-(2-hydroxyethyl)-5-nitrosoindoline | 80 | 86 |
| N,N-bis-(2-hydroxyethyl)-3-chloro-4-nitrosoaniline | 315 | 72 |
| 2,4-dimethoxy-nitrosobenzene | 130 | 95 |
| N,N-bis-(2-methoxyethyl)-4-nitrosoaniline | 245 | 68 |
| 3-methoxy-4-nitrosophenol | 140 | 30 |
| N-(2-hydroxyethyl)-6-nitroso-1,2,3,4-tetra-hydroquinoline | 95 | 82 |
| N,N-dimethyl-3-chloro-4-nitrosoaniline | 275 | 27 |
| N,N-bis-(2-hydroxyethyl)-3-fluoro-4-nitrosoaniline | 260 | 74 |
| N,N-bis-(2-hydroxyethyl)-3-methylthio-4-nitrosoaniline | 195 | 21 |
| N-(2-hydroxyethyl-N-2-(2-methoxyethoxy)ethyl)-4-nitrosoaniline | 210 | 59 |
| N-(2-hydroxyethyl)-N-(3-methoxy-2-hydroxy-1-propyl)-4-nitrosoaniline | 225 | 65 |
| N-(2-hydroxyethyl)-N-(3-(2-hydroxyethoxy-2-hydroxy-1-propyl)-4-nitrosoaniline | 210 | 54 |

[a]First peak potential of the electron carrier reduced with glucose oxidase and glucose in mV against Ag/AgCl
[b]Current of the first maximum in the cyclovoltammogram at 1 minute reaction time when compared with the current at 10 minutes reaction time in %.
[c]Concentration $5 \times 10^{-4}$ mol/l.

The cyclovoltammograms for N-(2-hydroxyethyl)-N'-p-nitrosophenyl-piperazine and N,N-bis-(2-hydroxyethyl)-p-nitrosoaniline are shown in FIG. 7. The cyclovoltammograms were measured with 10 mmol/l glucose in order to avoid interferences by reactions of residual glucose while recording the cyclovoltammogram.

EXAMPLE 7

Comparison of an electron carrier according to the present invention with one according to the state of the art a) In an experimental construction as described in Example 1, N-methyl-N'-(4-nitrosophenyl)-piperazine is used at a concentration of $10^{-4}$ mol/l in a phosphate buffer pH 7.0. Measurement of cyclovoltammograms at glucose concentrations between 0 and 3 mmol/l yields a dependence of the current density on the glucose concentration as shown in FIG. 8. At low concentrations it is seen that atmospheric oxygen has an influence which can be avoided by measurement under argon. The same result as that using argon as a protective gas is obtained when the electron carrier is used at a higher concentration ($10^{-2}$ mol/l). Influence of the measurement by oxygen can also be avoided by use of glucose dehydrogenase instead of glucose oxidase.

b) When tetrathiafulvalene is used as the electron carrier according to the state of the art instead of N-methyl-N'-(4-nitrosophenyl)-piperazine as the electron carrier according to the present invention, the dependence of the current density on the glucose concentration is as shown in FIG. 9. Tetrathiafulvalene shows a substantially higher interference by oxygen than is the case with the electron carrier according to the present invention. In addition, much lower current densities are measured.

Tetrathiafulvalene is very sparingly soluble. In order to obtain a concentration of $10^{31\ 4}$ mol/l in a phosphate buffer pH 7.0, 2.5% Tween 20[R] must be used as a detergent. Adjustment to much higher tetrethiafulvalene concentrations, as is possible in the case of the electron carrier according to the present invention, in order to reduce the oxygen interference, is not possible due to the sparing solubility.

EXAMPLE 8

Enzyme determination a) Lactate dehydrogenase test

The following solutions are prepared analogous to the test arrangement according to

EXAMPLE 1:

0.1 mol/l sodium phosphate buffer, 0.1 mol/l potassium chloride, pH 9.0.
10 mmol/l N,N-bis-(2-hydroxyethyl)-p-nitrosoaniline
0.1 mol/l D,L-lactate (sodium salt)
1 U/ml diaphorase from microorganisms
10 mmol/l NAD+.

Current is measured at a constant potential of 75 mV against silver/silver chloride while stirring vigorously (magnetic stirrer, 1000 rotations per minute). It is started by addition of lactate dehydrogenase (EC 1.1.1.27). Different amounts of lactate dehydrogenase are added and measurements are made in each case after 100, 200, 300, 400, 500 and 600 seconds. The current-/time curves obtained are shown in FIG. 10. The LDH activities plotted on the ordinate were determined according to the usual pyruvate reduction test.

b) Glucose dehydrogenase test

A test for AND-dependent glucose dehydrogenase can be carried out analogous to the description under a) in 0.1 mol/l potassium phosphate buffer, 0.1 mol/l potassium chloride, pH 7.0 with 10 mmol/l NAD+, 10 mmol/l electron carrier according to the present invention, 1 U/ml diaphorase and 0.1 mol/l glucose.

Oxidases, diaphorase or non-NAD-dependent dehydrogenases can be determined correspondingly.

Example 9

Disposable electrode system for the detection of glucose

A sensor electode system according to FIG. 4 is produced by mounting the working electrode (5), reference electrode (6), counterelectrode (7) and leads (55, 66, 77) on a polycarbonate foil (8) by means of screen printing using suitable printing pastes. The leads consist of commercial graphite printing paste (Acheson 421 SS, Deutsche Acheson Colloids, Ulm, German Federal Republic). The reference electrode (6) and the counterelectrode (7) consist of commercial silver conducting paste which is mixed with 20% by weight pulverized silver chloride (Acheson SS 24566, Deutsche Acheson Colloids. Ulm, German Federal Republic).

For the working electrode (5), 3 mmol/l N,N-bis-hydroxyethyl-p-nitrosoaniline, 500 KU glucose oxidase (glucose oxidase, degree of purity II, Boehringer Mannheim GmbH, Mannheim, German Federal Republic) per 100 g mixture, 30% by weight graphite powder (UF 296/97, Graphitwerke Kropfmuhl, German Federal Republic) and 4% by weight ethylene glycol are homogenized in a 2% by weight swelling mixture of hydroxyethyl cellulose (Natrosol 250 G, Hercules BV, Rijswijk, Netherlands) in 0.05 mol/l sodium phosphate buffer (pH 7.0). The areas of the electrodes are:

for the working electrode (5): $4 \times 6$ mm$^2$ = 24 mm$^2$,
for the reference electrode (6): $1 \times 1.5$ mm$^2$ = 1.5 mm$^2$ and
for the counterelectrode (7): $1 \times 1.5$ mm$^2$ = 1.5 mm$^2$.

The sensor electrode system produced by screen printing is immersed in a measuring solution which contains 0.05 mol/l sodium phosphate buffer (pH 7.0), 0.1 mol/l sodium chloride and 0-45 mmol/l glucose in such a way that the electrode surfaces are covered by the liquid to be examined. Current/time curves, which are shown in FIG. 11, are recorded at 200 mV potential against the integrated silver/silver chloride reference electrode (6). A plot of the values for current after 10 seconds measurement time yields the calibration curve shown in FIG. 12 which shows the dependence of the current flow on the glucose concentration.

EXAMPLE 10

Production of 2.2'-[(4-nitrosoaryl)imino]bis-ethanols 2 mol N,N-bis-(β-hydroxyethylaniline) (or its aryl-substituted analogues) is added in portions, while stirring vigorously, to a mixture of 200 ml water and 400 ml concentrated hydrochloric acid in a 4 l threenecked flask with stirrer, thermometer and dropping funnel. The resulting solution is cooled to 0° C. with a cold bath and a solution of 148 g (2.1 mol) sodium nitrite in 200 ml water is added dropwise within 20 minutes at 0° to 2° C. while stirring. It is then stirred for a further 30 minutes at 0° C., the mostly crystalline nitroso compound which has a yellow to green colour is aspirated and the filter cake is washed twice with 200 ml ice-cold, half-concentrated hydrochloric acid. For purification, the crude product is dissolved in 900 ml water, 400 ml concentrated hydrochloric acid is added while stirring vigorously, it is stirred for 30 minutes at room temperature, then for 30 minutes while cooling on ice. The crystallizate obtained is subsequently dissolved in 580 ml water to which 265 ml concentrated hydrochloric acid is added, and stirred for 30 minutes at room temperature and 30 minutes while cooling on ice. The crystals which form are aspirated, washed three times with 150 ml ice-cold acetone each time. twice with 200 ml diethylether each time and dried in a vacuum at room temperature. In this way the following are obtained:

a) 2,2'-[(4-nitrosophenyl)imido]bis-ethanol-hydrochloride

Yield 32.8% of theory, green crystals; m.p. 160° C. (decomp.).

Using corresponding aryl-substituted analogues the following are obtained analogously:

b) 2,2'-[(3-fluoro-4-nitrosophenyl)imino]bis-ethanol-hydrochloride

Yield: 26.5% of theory, yellow crystals; f.p. 140° C. (decomp.). TLC: silica gel 60 (Merck) - mobile phase: ethyl acetate/methanol = 5:1, $R_f$ = 0.59 from 3-fluoro-N,N-bis-[2-hydroxyethyl]aniline (Chem. Abstr. 57, 13922 [1962])

c) 2,2'-[(3-chloro-4-nitrosophenyl)imino]bis-ethanol-hydrochloride

Yield: 2% of theory, yellow crystals; m.p. 154° C. (decomp.). TLC: silica gel 60 (Merck) - mobile phase: methylene chloride/methanol = 5:1, $R_f$ = 0.72 from 3-chloro-N,N-bis-[2(hydroxyethyl]aniline (M. Freifelder, G. R. Stone, J. Org. Chem. 26, 1499 (1961))

d) 2,2'-(3-methoxy-4-nitrosophenyl)imino]bis-ethanol-hydrochloride

Yield: 32% of theory, ochre-coloured crystals; m.p. 145°-146° C. (decomp.). TLC: silica gel 60 (Merck) - mobile phase: methylene chloride/methanol = 5:1, $R_f$ = 0.4 from 3-methoxy-N,N-bis[2-hydroxyethyl]aniline (M. Freifelder et al., J. Org. Chem. 26, 1499 (1961))

e) 2,2'-[(3-methylmercapto-4-nitrosophenyl)imino]-bis-ethanol-hydrochloride

Yield: 59.3% of theory, red-brown crystals; m.p. 148° C. (decomp.). TLC: silica gel 60 (Merck) - mobile phase: ethyl acetate/methanol = 5:1, $R_f$ = 0.53 from 3-methylmercapto-N,N-bis-[2-hydroxyethyl]aniline (obtainable from: dissolve 0.1 mol 3-methylmercaptoaniline in 50 ml 4 N acetic acid and 0.35 mol ethylene oxide and stir for 12 hours at room temperature. Add excess NaHCO$_3$ solution, extract with methylene chloride and purify by column chromatography on silica gel 60 (Merck) - mobile pnase toluene / acetone = 5:2, $R_f$ = 0.18, yield 25%, colourless oil).

f) 2-[methyl(3-chloro-4-nitrosophenyl)amino]ethanol-hydrochloride

Yield: 15% of theory, yellow crystals; m. p. 147° C. (decomp.), TLC: silica gel 60 (Merck) - mobile phase: methylene chloride/methanol = 19:1, $R_f$ = 0.34 from 2-[methyl(3-chlorophenyl)amino ethanol (obtained from 2-[(3-chlorophenyl)amino]ethanol by boiling for 3 hours with methyliodide in the presence of 10% NaOH; purified by column chromatography on silica gel 60 (Merck) - mobile phase: toluene/acetone = 5:2, $R_f$ = 0.39, yield 25%, colourless oil).

EXAMPLE 11

2-[(2-hydroxyethoxy)-ethyl-(4-nitrosophenyl) amino]ethanol hydrochloride

A) 2-[(2-hydroxyethoxy)ethyl-(phenyl)amino]ethanol

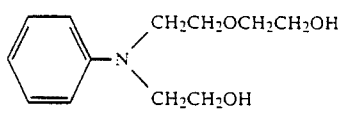

146 g (0.8 mol) 2-(2-anilionoethoxy)ethanol (obtained by reacting aniline with 2-(2-chloroethoxy)ethanol, yield 54%, colourless oil, b.p.$_1$ 131°-133° C.) is dissolved in 500 ml 4N acetic acid, cooled with a cold bath to 0° C. while stirring and 70.5 g, i.e. ca. 79 ml (1.6 mol), ethylenoxide is added dropwise within five minutes at 0°-10° C. After leaving it to stand for 12 hours at room temperature, 500 ml water is added, it is neutralised while stirring and carefully adding a total of 200 g NaHCO$_3$ in small portions. Afterwards the liberated base is extracted with 500 ml methylene chloride, shaken again three times with 250 ml methylene chloride each time, the organic phases are combined, dried over sodium sulphate, aspirated and concentrated in a vacuum. 178.2 g product is obtained. TLC silica gel 60 (Merck) - mobile phase: toluene/acetone=5:2, R$_f$=0.18

B) 2-[2-hydroxyethoxy)-ethyl-(4-nitrosophenyl) amino]ethanol hydrochloride

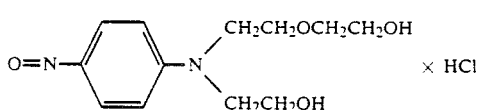

A mixture of 280 ml concentrated hydrochloric acid and 140 ml water is filled into a 2 l three-necked flask with stirrer, dropping funnel and thermometer, cooled down to −5° C. with a cooling bath of dry ice, 178 g (0.79 mol) of the substance obtained according to A) is added dropwise within 10 minutes at constant temperature and stirred for a further 15 minutes. A solution of 60 g (0.87 mol) sodium nitrite in 120 ml water is added to this at 0° C. whereby the solution becomes a blood-red to brown colour and it is stirred for a further 30 minutes at 0° C. Subsequently it is diluted by adding 500 ml water (pH of the reaction mixture 1.4) and 218 ml concentrated aqueous ammonia solution is added dropwise while cooling on ice at a maximum of 15° C. to pH 9. The liberated nitroso base is extracted five times with 400 ml n-butanol and the solvent is distilled off in a rotary evaporator. 212.8 g dark green oil is obtained. This is mixed with a mixture of 250 ml toluene/acetone=1:1 in order to remove inorganic products, the insoluble portion is aspirated and washed with 50 ml toluene/acetone=1:1. 18.4 g inorganic material remains as a residue. The filtrate is purified chromatographically on a silica gel 60 column (7.5 cm in diameter, filling level 90 cm, separating fluid toluene/acetone=1:1). 155 g nitroso base, dark green oil, is obtained. This is dissolved in 600 ml acetone and reacted dropwise with 250 ml saturated ethereal hydrochloric acid. After stirring for 30 minutes while cooling on ice the crystals which form are aspirated, washed three times with 100 ml acetone and dried in a vacuum at room temperature over diphosphorus pentoxide. 159.9 g (=69.6% of the theoretical yield) of the title compound is obtained; m.p. 118° C., TLC: silica gel 60 (Merck) - mobile phase: toluene/acetone=1:1, R$_f$=0.24.

EXAMPLE 12

The following compounds are produced in an analogous manner to Example 11:

a) 1-[N,N-(2-hydroxyethyl)-(4-nitrosoanilino)]-3-(2-hydroxyethoxy)-2-propanol hydrochloride

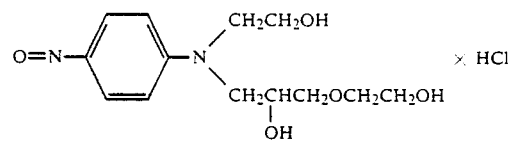

Yield: 10.5% of theory, orange coloured crystals, m.p. 104° C. (decomp.); TLC - silica gel 60 (Merck) - mobile phase: toluene/methanol=5:1, R$_f$=0.13 from 1-[N,N-(2-hydroxyethyl)(anilino)]-3-(2-hydroxyethoxy)-2-propanol

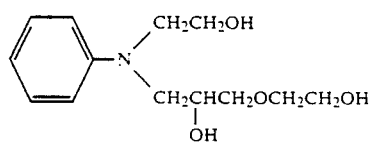

(this is from 1-[N-(anilino)]-3-(2-hydroxyethoxy)-2-propanol

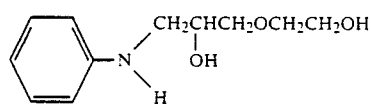

which is obtained from aniline with 1-chloro-3-(2-hydroxyethoxy)-2-propanol - yield: 21.5% colourless oil, TLC: silica gel 60 (Merck) - mobile phase: toluene/acetone=5:2, R$_f$=0.6) by reaction with ethylene oxide in the presence of 4 N acetic acid. 71% colourless oil, TLC: silica gel 60 (Merck) - mobile phase: toluene/acetone 5:2, R$_f$=0.43 b) 1-N-(2-hydroxyethyl)-(4-nitrosoanilino)]3-methoxy-2-propanol hydrochloride

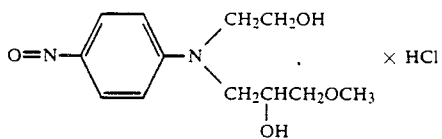

Yield: 44.5% light yellow crystals, m.p. 122° C. (decomp.). TLC: silica gel 60 (Merck) - mobile phase: methylene chloride/methanol=49:1, R$_f$=0.55 from (±)-3-[N-(2-hydroxyethyl)anilino]-1-methoxy-2-propanol (Deutsches Reichspatent 603808 (1933) - Friedländer 21, 295), (b.p.$_{11}$ 212°-214° C.).

c) 2-[(2-methoxyethoxy)ethyl-(4-nitrosophenyl) amino]ethanol

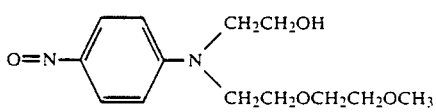

Yield: 25% of theory, dark brown resin. TLC: silica gel 60 (Merck) - mobile phase: methylene chloride/methanol=19:1, $R_f=0.49$; methylene chloride/methanol=5:1, $R_f=0.77$ (via the amorphous hygroscopic hydrochloride with $NH_3$);
from 2-[(2-methoxyethoxy)ethyl-(phenyl)-aminoethanol (A)

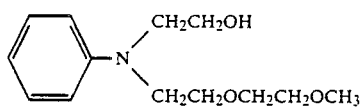

which was obtained from aniline and 2-methoxyethoxy-chloroethane (heat for one hour to 90° C. and separate by column chromatography on silica gel 60 (Merck) with toluene/ethyl acetate=5:1. The N-(2-methoxyethoxy-ethyl)aniline thus formed ($R_f=0.69$, colourless oil)

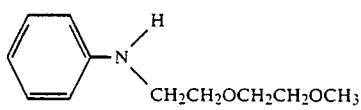

results in (A) as a colourless oil, TLC: silica gel 60 (Merck) - mobile phase: toluene/acetone=5:1, $R_f=0.31$, with ethylene oxide and 4 N acetic acid.

d) 2-[2-(2-(2-(2-methoxy)ethoxy)ethoxy)ethyl)-4-(nitroso-phenyl)amino]ethanol

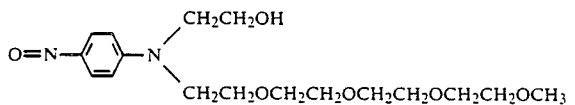

Yield 63% of theory, green oil, TLC: silica gel 60 (Merck) - mobile phase: toluene/acetone=1:5, $R_f=0.64$ from 2-[2-(2-(2-methoxy)ethoxy)ethoxy)ethyl)-4-(phenyl)amino]ethanol.

The starting compound was produced as follows: 20.5% of the theoretical yield of a yellow oil, $R_f=0.5$

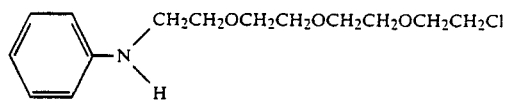

is obtained from aniline and diethylglycol-bis-(2-chloroethylether) (Perry, Hibbert Can. J. Res. 14, 81 (1936) by heating to 140° C. for four hours and subsequent separation by column chromatography on silica gel 60 (Merck) with toluene/ethyl acetate=2:1.

Its reaction with ethylene oxide in 4 N acetic acid yields almost quantitatively

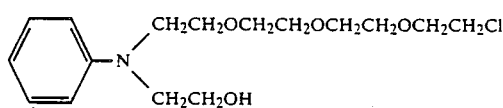

as a beige coloured oil, TLC: silica gel 60 (Merck) - mobile phase: methylene chloride/methanol=19:1, $R_f=0.61$.

Using $NaOCH_3$ in methanol (heat for 24 hours under reflux, evaporate, add water, take up in ethyl acetate and subsequently purify the crude product by column chromatography on silica gel 60 (Merck) with toluene/acetone=5:2), 51.3% of the theoretical yield of product is obtained as a colourless oil, $R_f=0.21$.

Example 13

N-(4-nitrosophenyl)-N-(2-diethylamino)-ethyl]-N,N'-diethyl-1,2-ethane-diamine-tris-hydrochloride

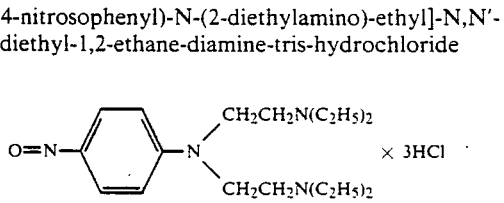

m.p. 125° C. (decomp.), TLC: silica gel 60 (Merck) - mobile phase: isopropanol/n-butyl-acetate/water/concentrated aqueous $NH_3=50:30:15:5$, $R_f=0.56$ from N-[di-(2-diethylamino)ethyl]aniline.

EXAMPLE 14

Production of 1-N-substituted 4-(4-nitrosophenyl)piperazines

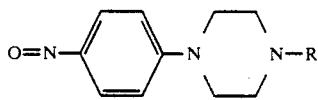

a) 1-methyl-4-(4-nitrosophenyl)-piperazinedihydrochloride

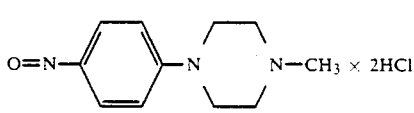

17.62 g (0.1 mol) 1-methyl-4-phenyl-piperazine (40.1% of the theoretical yield, b.p.$_{0.05}$ 82°-84° C., $R_f=0.31$, is obtained as a colourless liquid from 0.3 mol 1-phenyl-piperazine by heating to 150° C. for four hours with 0.2 mol tri-methyl phosphate, isolation by adding NaOH and extracting with diethylether and purifying by column chromatography on silica gel 60 (Merck) with methylene chloride/methanol=5:1, (according to Stewart et al., J. Org. Chem. 13, 134 (1948)) is dissolved in a mixture of 20 ml concentrated hydrochloric acid and 10 ml water, then a solution of 8 g (0.12 mol) sodium nitrite in 16 ml water is added dropwise at 0°14 2° C. within 15 minutes and it is stirred for a further 30 minutes at 10° C. 60 ml concentrated aqueous ammonia is added at the same temperature while cooling further, it is diluted by addition of 100 ml water and the redbrown solution (pH 9) is extracted three times by shaking with 100 ml methylene chloride each time, the organic phase is dried over $Na_2SO_4$, aspirated and evaporated. The residue (20.6 g moss-green crystals) is taken up in 40 ml methanol and reacted with 20 ml saturated ethereal hydrochloric acid while cooling. 15.8 g=56.8% of the theoretical yield of moss-green crystals of the title compound is obtained after aspirating and washing twice with 20 ml ether. m.p. 187°-189° C. (decomp.), TCL: silica gel 60 (Merch)–mobile phase: methylene chloride/methanol=5:1, $R_f=0.72$.

The following are prepared analogously:

b) 4-(4-nitrosophenyl)-1-piperazine-ethanoldihydrochloride

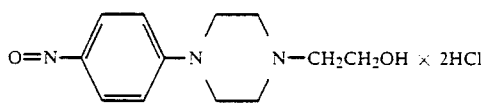

from 2-(4-phenyl-piperazino)-ethanol (Kremer, J. Amer. Chem. Soc. 58, 379 (1963)) as light grey crystals; purified by recrystallization from methanol/water=7:1, m.p. 170°-173° C. (decomp.), TLC: silica gel 60 (Merck) - mobile phase: methylene chloride/methanol=5:1, $R_f=0.67$ c) 3-[4-(4-nitrosophenyl)-1-piperazinyl]-1,2-propanediol-dihydrochloride

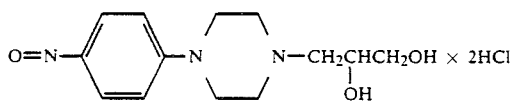

from 1-phenyl-4-(2,3-dihydroxypropyl)-piperazine (H. Howell et al., J. Org. Chem. 27, 1711 (1962)) as green Crystals, m.p. 163° C. (decomp.)- TLC: silica gel 60 (Merck), mobile phase: ethyl acetate/methanol=2:1, $R_f=0.41$.

4-(4-nitrosophenyl)-α-(methoxymethyl)-piperazine-1-ethanol-dihydrochloride

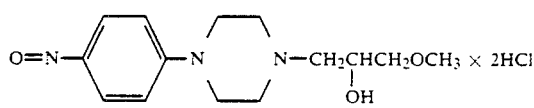

from 1-phenyl-4-(2-hydroxy-3-methoxypropyl)-piperazine (H. Howell et al., J. Org. Chem. 27, 1711 (1962)) as yellow crystals, m.p. 162° C. (decomp.) - TLC: silica gel 60 (Merck), mobile pnase: methylene chloride/methanol=19:1, $R_f=0.51$ e) 2-2-[4(4-nitrosophenyl)-1-piperazinyl]ethoxy]ethanol-dihydrochloride

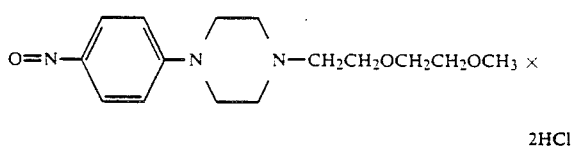

from 2-[2-[4-(phenyl)-1-piperazinyl]ethoxy-ethanol (obtained from 2 mol 1-phenylpiperazine and 1-[2-chloroethoxy]-2-methoxyethane (the latter according to U.S. Pat. No. 2,837,574) as green crystals, m.p. 134° C. (decomp.) - TLC: silica gel 60 (Merck) - mobile phase: ethyl acetate/methanol=5:1, $R_f=0.31$.

f) 1-(1,4-dioxanylyl)methyl-4-(4-nitrosophenyl)piperazine-dihydrochloride

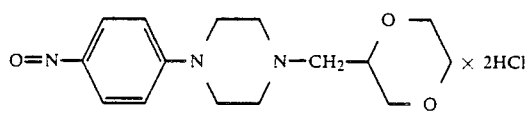

from 1-(1,4-dioxanylyl)methyl-4-(phenyl)-piperazine (obtained by heating 1-chloro-3-(β-hydroxyethoxy)-2-propanol (M. S. Kharash, W. Nudenberg, J. Org. Chem. 8, 189 (1943) for five hours with 1-phenylpiperazine to 130° C., extracting with ethyl acetate and evaporating. Purification by column chromatography on silica gel 60 (Merck) - mobile phase: toluene/acetone=5:2) as green yellow crystals, m.p. 166° C. (decomp.), TLC: silica gel 60 (Merck) - mobile phase: toluene/methanol=5:1, $R_f=0.69$.

EXAMPLE 15

Nitrosoheterocycles a) 5-nitroso-1-indolinoethanol hydrochloride

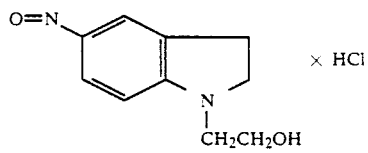

The nitroso compound is obtained from 1-indolinoethanol (obtained by heating 1 mol indoline with 1 mol 2-chloroethanol in the presence of 1 mol finely powdered $K_2CO_3$ under reflux yielding 63.8% of the theoretical yield of a colourless oil, $b.p._{0.1}$ 128°-130° C., TLC: silica gel 60 (Merck) - mobile phase: toluene/acetone=2, $R_f=0.42$) and is isolated as a base after addition of ammonia with methylene chloride. It is converted into the hydrochloride with ethereal hydrochloric acid. Light brown crystals are obtained. m.p. 180° C., TLC: silica gel 60 (Merck) - mobile phase: methylene chloride/methanol=5:1, $R_f=0.51$ b) 1-methyl-6-nitroso-1,2,3,4-tetrahydroquinoline hydrochloride

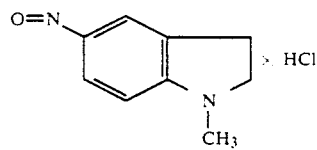

The title compound is prepared from 1-methyl1,2,3,4-tetrahydroquinoline (obtained from 1,2,3,4tetrahydroquinoline by heating with trimethylphosphate (according to Huisgen et al., Chem. Ber. 92, 203 (1959)). The crude product is produced in the usual manner analogous to Examples 10 and 11 and purified on silica gel 60 (Merck) with isopropanol/n-butylacetate/water=5:3:2. The title compound is obtained by dissolving this in acetone after addition of ethereal hydrochloric acid, m.p. 123°-124° C. (decomp.), TLC: silica gel 60, mobile phase: isopropanol/n-butylacetate/water=5:3:2, $R_f=0.7$.

c) 6-nitroso-3,4-dihydro-1(2H)-quinoline-ethanol hydrochloride

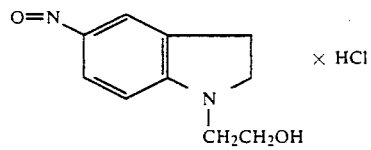

The title compound is obtained from 2-(3,4 dihydro-2H-quinolin-1-yl)ethanol (Zaheer et al., Indian J. Chem. 1, 479 (1963), $b.p._5$ 140°-144° C.). The crude product is purified by column chromatography on silica gel 60 (Merck), mobile phase: methylene chloride/methanol=19:1. 10.5% of the theoretical yield of ochre-coloured crystals of the title compound are obtained by precipitation of the hydrochloride from isopropanol with ethereal hydrochloric acid and recrystallizing from ethanol, m.p. 193°–195° C. (decomp.), TLC: silica gel 60 (Merck) - mobile phase: methylene chloride/methanol=19:1, $R_f$=0.36.

We claim:

1. A method for the electrochemical determination of an analyte in the presence of an oxidoreductase and a reducible substance which transfers electrons which arise during the course of the determination reaction from the oxidoreductase onto an electrode and thus leads to a signal which is a measure for the analyte to be determined whereby the reducible substance is enzymatically reduced and oxidized at the electrode in an overall irreversible reaction, wherein the substance which forms at the electrode by oxidation is an oxidized form of the enzymatically reduced substance other than the reducible substance used initially.

2. The method of claim 1, wherein said substance which forms at the electrode by oxidation is subsequently reduced by said oxido-reductase.

3. The method of claim 1, wherein said reducible substance accepts electrons arising during the course of the determination reaction from the oxidoreductase, thereby forming an electron-rich aromatic amine.

4. The method of claim 3, wherein said reducible substance is selected from the group of compounds of the formula I

     (I)

in which
R represents an aromatic residue which is more electronegative than aniline, and
X represents NO or NHOH,
and compounds of the formula II

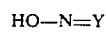     (II)

in which Y represents a quinoid system.

5. The method of claim 1, wherein the oxidoreductase is selected from the group consisting of an oxidase, a non-NAD(P)-dependent dehydrogenase and diaphorase.

6. A method for the electrochemical determination of an oxidoreductase in the presence of a corresponding enzyme substrate and a reducible substance which is capable of transferring electrons from the oxidoreductase onto an electrode and thus leads to a signal which is a measure for the enzyme to be determined, whereby the reducible substance is enzymatically reduced and oxidized at the electrode in an overall irreversible reaction, wherein the substance which forms by oxidation at the electrode is an oxidized form of the enzymatically reduced substance other than the reducible substance used initially.

7. A method for the electrochemical determination of an analyte, comprising
contacting a sample containing said analyte with an oxidoreductase and a reducible substance which transfers electrons which are generated by the oxidation of said analyte onto an electrode;
oxidizing said analyte with said oxidoreductase to produce a reduced enzyme;
enzymatically reducing said reducible substance by said reduced enzyme to produce a reduced substance and regenerate said oxidoreductase,
oxidizing said reduced substance at an electrode, thereby transferring electrons generated by the oxidation of said analyte to said electrode, wherein said oxidation of said reduced substance forms a substance which is different from said reducible substance, wherein the overall reaction is irreversible.

8. The method of claim 7, wherein said reducible substance is selected from the group consisting of N,N-bis-(2-hydroxyethyl) nitrosoaniline and N-(2-hydroxyethyl)-N-(2-(2-hydroxyethyoxy-4-nitrosoaniline.

9. A method for the electrochemical determination of an oxidoreductase, comprising
contacting a sample containing said oxidoreductase in the presence of a corresponding enzyme substrate with a reducible substance which transfers electrons which are generated by the oxidation of said enzyme substrate onto an electrode;
enzymatically reducing said reducible substance by said oxidoreductase to produce a reduced substance,
oxidizing said reduced substance at an electrode, thereby transferring electrons generated by the reduction of said reducible substance to said electrode, wherein said oxidation of said reduced substance forms a substance which is different from said reducible substance, wherein the overall reaction is irreversible.

* * * * *